(12) United States Patent
Heuscher et al.

(10) Patent No.: US 10,653,371 B2
(45) Date of Patent: *May 19, 2020

(54) GRATED COLLIMATION SYSTEM FOR COMPUTED TOMOGRAPHY

(71) Applicant: University of Utah Research Foundation, Salt Lake City, UT (US)

(72) Inventors: Dominic Heuscher, Salt Lake City, UT (US); Frederic Noo, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 748 days.

This patent is subject to a terminal disclaimer.

(21) Appl. No.: 14/848,102

(22) Filed: Sep. 8, 2015

(65) Prior Publication Data

US 2016/0000389 A1    Jan. 7, 2016

Related U.S. Application Data

(63) Continuation of application No. 13/531,472, filed on Jun. 22, 2012, now Pat. No. 9,125,572.

(51) Int. Cl.
*A61B 6/06* (2006.01)
*G21K 1/04* (2006.01)
(Continued)

(52) U.S. Cl.
CPC ............ *A61B 6/4035* (2013.01); *A61B 6/027* (2013.01); *A61B 6/032* (2013.01); *A61B 6/06* (2013.01);
(Continued)

(58) Field of Classification Search
CPC ........... A61B 6/027; A61B 6/032; A61B 6/06; A61B 6/4035; A61B 6/469; A61B 6/481;
(Continued)

(56) References Cited

U.S. PATENT DOCUMENTS 3,936,647 A    2/1976 Fekete
4,868,842 A    9/1989 Dowd
(Continued)

FOREIGN PATENT DOCUMENTS

| WO | WO 2012/032435 A1 | 3/2012 |
| WO | WO 2013/127005 A1 | 9/2013 |
| WO | WO 2014/047518 A1 | 3/2014 |

OTHER PUBLICATIONS

Christner et al.; Dose Reduction in Helical CT: Dynamically Adjustable z-Axis X-Ray Beam Collimation; American Journal of Roentgenology; Jan. 2010; pp. W49-W55; vol. 194; American Roentgen Ray Society.
(Continued)

*Primary Examiner* — Glen Kao
(74) *Attorney, Agent, or Firm* — Thorpe North & Western, LLP

(57) ABSTRACT

A collimator for a computed tomography imaging device can include first and second leaves positioned on opposing sides of a primary radiation delivery window. The first and second leaves can include first and second gratings having a plurality of attenuating members with a plurality of secondary radiation delivery windows extending between adjacent attenuating members.

23 Claims, 19 Drawing Sheets

(51) Int. Cl.
*A61B 6/00* (2006.01)
*A61B 6/02* (2006.01)
*A61B 6/03* (2006.01)
*G21K 1/02* (2006.01)

(52) U.S. Cl.
CPC .............. *A61B 6/507* (2013.01); *A61B 6/542* (2013.01); *A61B 6/469* (2013.01); *A61B 6/481* (2013.01); *A61B 6/488* (2013.01); *A61B 6/5205* (2013.01); *G21K 1/025* (2013.01)

(58) Field of Classification Search
CPC ....... A61B 6/488; A61B 6/507; A61B 6/5205; A61B 6/542; G21K 1/025; G21K 1/02; G21K 1/04; G21K 1/046
See application file for complete search history.

(56) References Cited

U.S. PATENT DOCUMENTS

| | | | |
|---|---|---|---|
| 5,187,659 | A | 2/1993 | Eberhard et al. |
| 5,379,333 | A | 1/1995 | Toth |
| 5,822,393 | A | 10/1998 | Popescu |
| 6,091,798 | A | 7/2000 | Nygren et al. |
| 6,125,167 | A | 9/2000 | Morgan |
| 6,445,761 | B1 | 9/2002 | Miyazaki et al. |
| 6,480,565 | B1 | 11/2002 | Ning |
| 6,483,981 | B1 | 11/2002 | Krahn |
| 6,931,100 | B2 | 8/2005 | Kato et al. |
| 7,086,780 | B2 | 8/2006 | Wu et al. |
| 7,242,749 | B2 | 7/2007 | Hsieh et al. |
| 7,564,937 | B2 | 7/2009 | Nakanishi |
| 8,031,828 | B1 | 10/2011 | DeMan et al. |
| 8,184,775 | B1 | 5/2012 | Fan et al. |
| 8,213,568 | B2 | 7/2012 | Heuscher et al. |
| 8,571,172 | B2 | 10/2013 | Dafni et al. |
| 8,693,621 | B2 | 4/2014 | Thran et al. |
| 9,125,572 | B2 * | 9/2015 | Noo ................. A61B 6/027 |
| 2001/0005409 | A1 | 6/2001 | Gohno et al. |
| 2002/0126798 | A1 | 9/2002 | Harris |
| 2002/0131556 | A1 | 9/2002 | Steinberg |
| 2004/0081270 | A1 | 8/2004 | Heuscher |
| 2006/0034419 | A1 | 2/2006 | Nishide et al. |
| 2006/0067481 | A1 | 3/2006 | Morton |
| 2007/0019783 | A1 | 1/2007 | Hockersmith et al. |
| 2007/0064876 | A1 | 3/2007 | Hoffman |
| 2007/0140423 | A1 | 6/2007 | Foland |
| 2007/0276215 | A1 | 11/2007 | Ziegler |
| 2008/0205723 | A1 | 8/2008 | Bredno et al. |
| 2008/0317198 | A1 | 12/2008 | Thornton |
| 2009/0202035 | A1 | 8/2009 | Tsukagoshi |
| 2009/0252285 | A1 | 10/2009 | Shapiro et al. |
| 2009/0285355 | A1 | 11/2009 | Brada et al. |
| 2010/0054395 | A1 | 3/2010 | Noshi et al. |
| 2010/0091937 | A1 | 4/2010 | Raupach |
| 2010/0239063 | A1 | 9/2010 | Pietig et al. |
| 2010/0246752 | A1 | 9/2010 | Heuscher et al. |
| 2010/0274120 | A1 | 10/2010 | Heuscher |
| 2010/0310037 | A1 | 12/2010 | Wang et al. |
| 2011/0007878 | A1 | 1/2011 | Dafni et al. |
| 2011/0013742 | A1 | 1/2011 | Zaiki et al. |
| 2011/0058645 | A1 | 3/2011 | Heuscher |
| 2011/0317814 | A1 | 12/2011 | Verman |
| 2013/0156149 | A1 | 6/2013 | Kohara |
| 2013/0272504 | A1 | 10/2013 | Deutsch |
| 2013/0343513 | A1 | 12/2013 | Noo et al. |
| 2013/0343518 | A1 | 12/2013 | Noo et al. |
| 2014/0086380 | A1 | 3/2014 | Song et al. |
| 2014/0146948 | A1 | 5/2014 | Zhang et al. |
| 2014/0169519 | A1 | 6/2014 | Bergfjord et al. |
| 2014/0177782 | A1 | 6/2014 | Herold |

OTHER PUBLICATIONS

Graves et al.; Variable aperture collimator for small animal radiotherapy; Medical Physics; Nov. 2007; pp. 4359-4367; Med. Phys. 34 (11); Stanford, California.

Heuscher et al.; CT Dose Reduction Using Dynamic Collimation; IEEE Nuclear Science Symposium Conference Record; Oct. 2011; pp. 3470-3473; IEEE.

Liu et al.; Renal Perfusion and Hemodynamics: Accurate in Vivo Determination at CT with a 10-Fold Decrease in Radiation Dose and HYPR Noise Reduction; Radiology; Oct. 2009; pp. 98-105; vol. 253, No. 1; RSNA.

Poulsen et al.; DMLC motion tracking with a single imager; Int. J. Radiation Oncology Biol. Phys.; 2010; pp. 600-607; vol. 77, No. 2; Elsevier Inc. Stanford, California.

* cited by examiner

Fig. 11
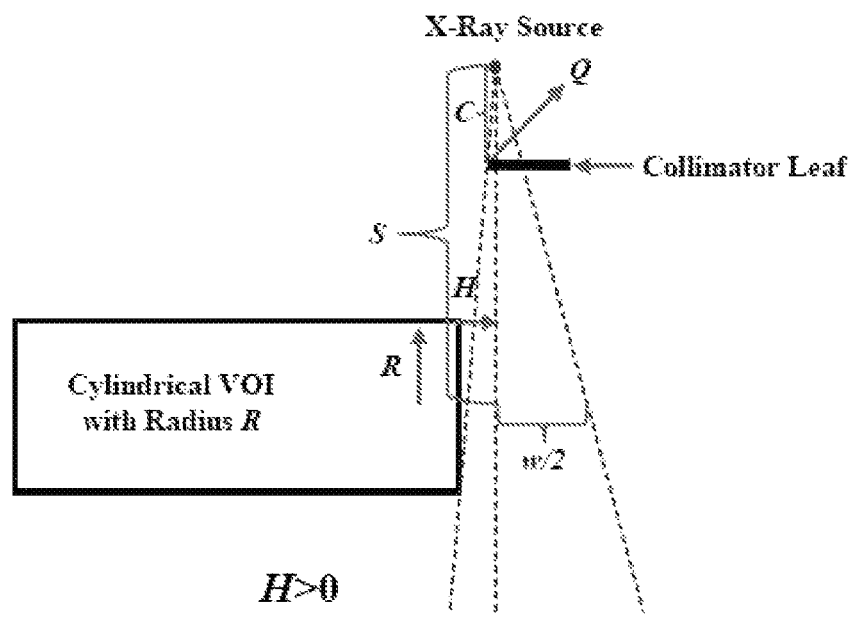
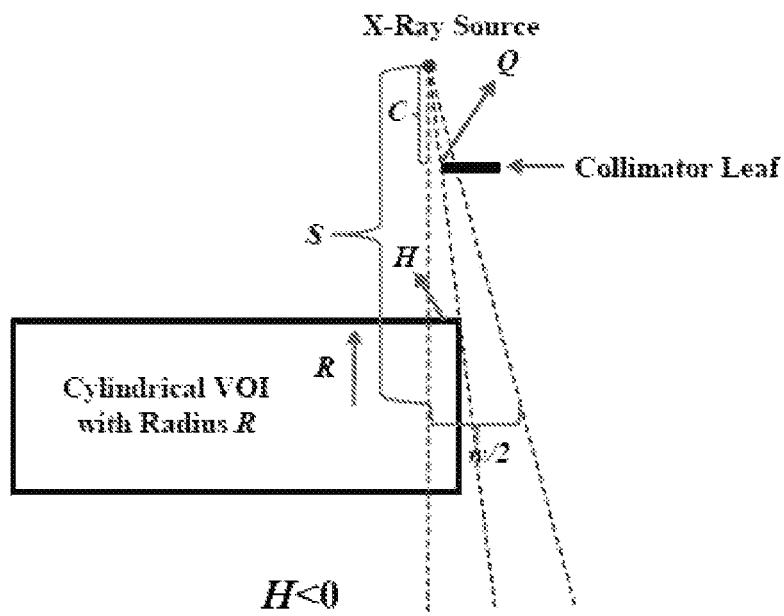
Fig. 12

Fig. 13
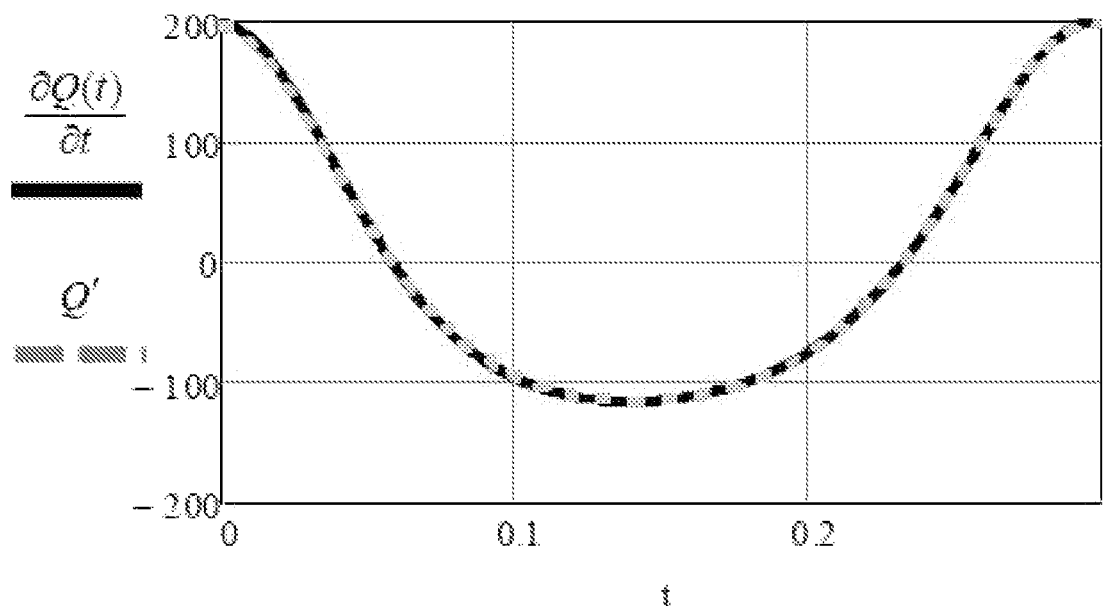
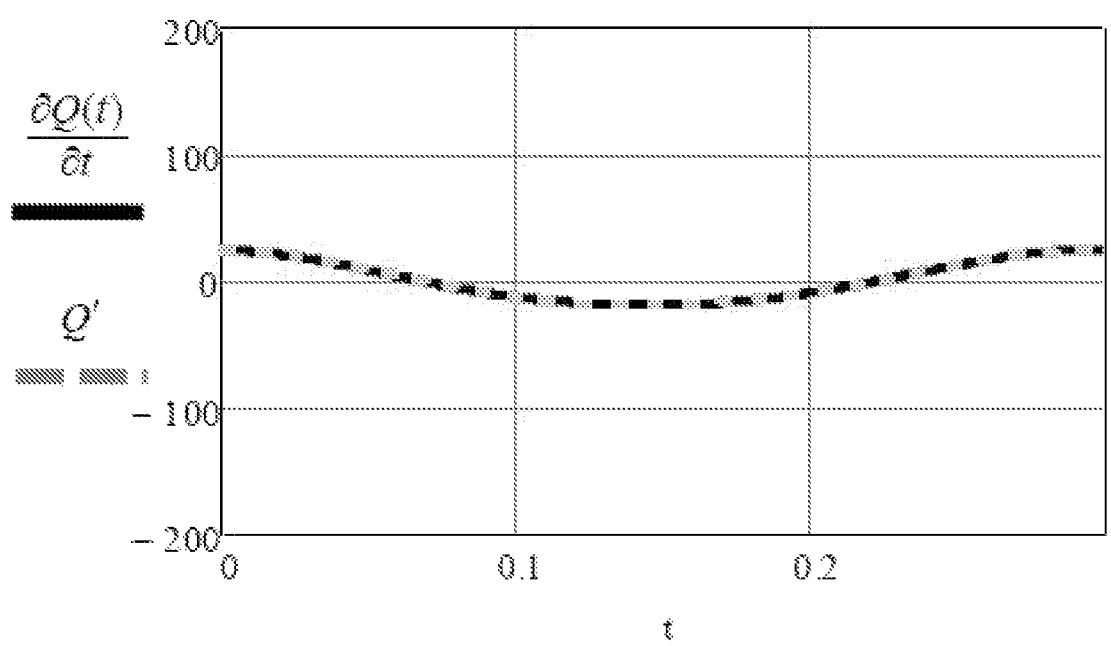
Fig. 14

GRATED COLLIMATION SYSTEM FOR COMPUTED TOMOGRAPHY

RELATED APPLICATION

This application is a continuation application of U.S. application Ser. No. 13/531,472, filed Jun. 22, 2012, now issued as U.S. Pat. No. 9,125,572, which is incorporated herein by reference.

GOVERNMENT INTEREST

This invention was made with government support under R01 EB007168 and R21 EB007236 awarded by the National Institutes of Health. The Government has certain rights to the invention.

FIELD

The subject technology relates generally to radiological devices and methods and, in some embodiments, more particularly to devices and methods for computed tomography (CT).

BACKGROUND

CT systems have included single-slice and multiple-slice detectors. CT systems with multiple-slice detectors are, in particular, able scan large volumes of interest. Some large volumes are imagined by helical CT scanning. In helical scanning, the subject moves axially relative to a radiation beam such that the beam traverses a helical path through the subject. Such scanning can be leveraged to quickly scan whole or large portions of organs.

SUMMARY

An aspect of at least one embodiment disclosed herein includes the realization that high radiation dose of conventional perfusion CT imaging and the lack of standardized perfusion CT imaging protocols limit the clinical potential of CT. Some embodiments disclosed herein significantly reduce the x-ray dose of CT perfusion scans without sacrificing clinical accuracy. Some embodiments that significantly reduce the x-ray dose of CT perfusion scans without sacrificing clinical accuracy, thereby expand use of perfusion CT as a diagnostic tool. Some embodiments of devices and methods for perfusion CT imaging can be used for diagnosis, treatment of diseases, or both. In various embodiments, a radiation dose delivered to a subject can be reduced by application of any one of a transverse dynamic collimator, a grated collimator, an adaptive sampling algorithm, or an adaptive exposure algorithm, or a combination of some or all thereof. Some embodiments can be used for perfusion imaging of the kidneys, pancreas, liver, and heart.

Primarily due to concerns about the magnitude of radiation dose delivered, perfusion CT imaging has not been used routinely in various fields, including stroke assessment, oncology, and cardiac and kidney function. In some embodiments, reduction of radiation dose delivered to a subject can permit application of perfusion CT to those applications wherein dose is a limiting factor, e.g. cardiac perfusion. Although some embodiments are discussed herein with respect to perfusion CT imaging, some embodiments can be used with other imaging. Similarly, although some embodiments may provide particular benefits for perfusion CT imaging, various embodiments can provide advantages with other imaging.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

1. A collimator for a computed x-ray tomography imaging device, comprising a first grating and a second grating positioned on opposing sides of a primary radiation delivery window, each of the first and second gratings comprising a plurality of attenuating members with a plurality of secondary radiation delivery windows extending between adjacent attenuating members of the first grating and the second grating, respectively.

2. The collimator of clause 1, wherein a width of each secondary windows is less than a width of the primary window.

3. The collimator of clause 1, wherein a total area of each of the plurality of secondary windows is less than a total area of the primary window.

4. The collimator of clause 1, wherein a width of each secondary window is proportional to a distance between the secondary window and the primary window.

5. The collimator of clause 4, wherein the width of each secondary window is linearly proportional to the distance between the secondary window and the primary window.

6. The collimator of clause 4, wherein the width of each secondary window is positively proportional to the distance between the secondary window and the primary window.

7. The collimator of clause 1, wherein a width of each attenuating member is proportional to a distance between the attenuating member and the primary window.

8. The collimator of clause 7, wherein the width of each attenuating member is linearly proportional to the distance between the attenuating member and the primary window.

9. The collimator of clause 7, wherein the width of each attenuating member is positively proportional to the distance between the attenuating member and the delivery window.

10. The collimator of clause 1, wherein the secondary windows comprise open passages extending through the grating.

11. The collimator of clause 1, wherein the secondary windows comprise panes of substantially radio-transmissive material.

12. The collimator of clause 1, wherein the attenuating members are oriented generally parallel to sides of the primary window.

13. The collimator of clause 1, wherein the secondary windows are oriented generally parallel to sides of the primary window.

14. The collimator of clause 1, wherein the first grating is movable relative to the second grating.

15. The collimator of clause 14, wherein the first and second gratings are independently movable.

16. The collimator of clause 1, wherein the attenuating members of the first grating are integrally formed with each other, and the attenuating members of the second grating are integrally formed with each other.

17. The collimator of clause 16, wherein the attenuating members of the first grating are integrally formed with the attenuating members of the second grating.

18. A method of directing radiation during computed tomography (CT) imaging, comprising:
   emitting x-ray radiation from a radiation source toward an object;
   passing a first portion of the radiation through a primary window toward a target region in the object;
   passing a second portion of the radiation through at least one secondary window, on each of opposing sides of the primary window, to corresponding regions in the object outside the target region;
   attenuating, between the primary and secondary windows, at least a third portion of the radiation; and
   generating CT image data based on the first and second portions of the radiation.

19. The method of clause 18, further comprising rotating the radiation source and the primary and secondary windows about an axis, and wherein radiation is passed through the primary window and the secondary windows while either (i) centers of the primary window and at least two of the secondary windows lie in a plane non-parallel to the axis or (ii) a plane intersecting the centers and the axis is non-parallel to the axis.

20. The method of clause 18, further comprising rotating the radiation source and the primary and secondary windows about an axis, and translating the secondary windows relative to the primary window in a direction non-parallel to the axis.

21. The method of clause 20, wherein the secondary windows are translated relative to the primary window during rotation of the radiation source.

22. The method of clause 21, wherein a first of the secondary windows is translated independently of a second of the secondary windows on an opposing side of the primary window from the first of the secondary windows.

23. The method of clause 18, wherein the attenuating comprises blocking passage of at least the third portion of the radiation between the primary and secondary windows.

24. A computed tomography device, comprising:
   a gantry configured to rotate about an axis and comprising an opening configured to accommodate an object;
   a radiation source mounted to the gantry;
   a collimator positioned between the radiation source and the gantry opening, the collimator comprising first and second leaves respectively bounding first and second opposing sides of a radiation delivery window, the first leaf and the second leaf being movable to adjust at least one of a size or a location of the radiation delivery window relative to the radiation source in a direction non-parallel to the axis.

25. The computed tomography device of clause 24, wherein the first leaf is moveable independently of the second leaf.

26. The computed tomography device of clause 24, further comprising third and fourth leaves respectively bounding third and fourth opposing sides of the window and aligned with the window along the axis.

27. The computed tomography device of clause 26, wherein each of the first and second sides is substantially orthogonal to each of the third and fourth sides.

28. The computed tomography device of clause 24, wherein the collimator is mounted within about 27 cm of the radiation source.

29. The computed tomography device of clause 24, wherein the collimator is mounted within about 12 cm of the radiation source.

30. A computed tomography device, comprising:
   a gantry configured to rotate about an axis and comprising an opening configured to accommodate an object;
   a radiation source mounted to the gantry;
   a collimator positioned between the radiation source and the gantry opening, the collimator comprising a first leaf and a second leaf respectively bounding first and second opposing sides of a radiation delivery window, the first leaf and the second leaf being independently movable relative to the radiation source in a direction non-parallel to the axis.

31. The device of clause 30, wherein the first leaf and the second leaf are independently movable relative to the radiation source in a direction tangential to a circle (i) centered on the axis and (i) defining a plane that is not parallel to the axis.

32. The device of clause 31, wherein the first leaf is independently movable relative to the second leaf.

33. A method of radiologic imaging, comprising:
   rotating, about an axis, a gantry carrying a radiation source;
   emitting radiation from the radiation source toward an object between a pair of leaves;
   during rotation of the gantry, moving the pair of leaves relative to the radiation source in a direction nonparallel to the axis.

34. The method of clause 33, further comprising:
   performing a preliminary scan of a object;
   demarcating a region of interest in the object, based on the preliminary scan, that is at least one of (i) non-concentric with the axis or (ii) non-circular; and
   controlling movement of the pair of leaves during rotation of the gantry to adjust at least one of a location, relative to the radiation source, or a dimension, of a radiation delivery window such that substantially only the region of interest is exposed to radiation through the radiation delivery window.

35. The method of clause 34, further comprising directing radiation through a plurality of secondary windows, on opposing sides of the radiation delivery window, to regions in the object outside the region of interest; and substantially blocking the passage of radiation toward the object in regions between the radiation delivery window and the secondary windows.

36. The method of clause 33, further comprising repositioning the object such that a region of interest is located closer to the axis.

37. A method of contrast-enhanced computed tomography (CT) imaging, comprising:
   (a) repeatedly scanning a target region at a frequency during a session, the scanning comprising performing a CT scan by emitting x-ray radiation toward the target region, the frequency initially being a first rate;
   (b) monitoring, during the session, an indicator of attenuation of radiation by a contrast-enhanced first structure within the target region;
   (c) after detecting an increase of the attenuation, increasing the frequency to a second rate; and
   (d) after detecting a decrease in the attenuation after (c), decreasing the frequency to a third rate.

38. The method of clause 37, further comprising generating a representation of a relationship between time and radiation attenuation by a second structure within the target region.

39. The method of clause 38, wherein the radiation attenuation by the second structure with respect to time represents an indicator of vascular perfusion of the second structure.

40. The method of clause 37, further comprising monitoring of a rate of change of the attenuation.

41. The method of clause 40, wherein the frequency is increased to the second rate in response to detection of a decrease in a rate at which the attenuation is increasing.

42. The method of clause 41, further comprising beginning monitoring of the rate of change after detecting an increase of the attenuation to or beyond a threshold.

43. The method of clause 42, wherein the threshold is about 35 HU.

44. The method of clause 42, wherein the threshold comprises a degree of increase in the attenuation compared to a value indicated by an initial scan.

45. The method of clause 40, further comprising decreasing the frequency below the third rate in response to detection of a decrease in a rate at which the attenuation is decreasing.

46. The method of clause 45, wherein decreasing the frequency below the third rate comprises reducing the frequency with each successive scan.

47. The method of clause 46, wherein the frequency is approximately halved with each successive scan.

48. The method of clause 37, wherein the frequency is reduced to the third rate upon a first detection of a decrease in attenuation after (c).

49. The method of clause 37, wherein the first rate is one scan approximately every two seconds.

50. The method of clause 37, wherein the second rate is one scan approximately every second.

51. The method of clause 37, wherein the third rate is one scan approximately every two seconds.

52. The method of clause 37, wherein the structure comprises at least one of a heart chamber, an aorta, or another blood vessel.

53. The method of clause 37, further comprising terminating the scanning after a predetermined period of time and performing a final scan at the end of the predetermined period.

54. The method of clause 37, further comprising terminating the scanning after a predetermined period of time, and, if a remaining time between a latest scan and an end of the predetermined period is less than an interval between the latest scan and an immediately preceding scan, performing (i) a penultimate scan at approximately half of the remaining time after the latest scan and (ii) a final scan at the end of the predetermined period.

55. A computer-implemented system for controlling contrast-enhanced computed tomography imaging, comprising:
an attenuation monitoring module configured to monitor, during an imaging session, an indicator of attenuation of radiation by a contrast-enhanced structure within a target region;
a scanning-frequency control module configured to (i) increase a frequency of scanning from a first rate to a second rate after detection of an increase of the attenuation, and (ii) decrease the frequency to a third rate after detecting a decrease in attenuation after increasing the frequency to the second rate.

56. The computer-implemented system of clause 55, wherein the monitoring module is further configured to monitor a rate of change of the attenuation.

57. The computer-implemented system of clause 56, wherein the scanning-frequency control module is further configured to increase the frequency to the second rate in response to detection of a decrease in a rate at which the attenuation is increasing.

58. The computer-implemented system of clause 56, wherein the monitoring module is further configured to begin monitoring of the rate of change after detection of compliance of the attenuation with a threshold.

59. The computer-implemented system of clause 58, wherein the threshold is 35 HU.

60. The computer-implemented system of clause 58, wherein the threshold is a degree of increase in the attenuation compared to a value indicated by an initial scan.

61. The computer-implemented system of clause 55, further comprising a processing module configured to generate a representation of a relationship between time and radiation attenuation by a second structure within the target region.

62. The computer-implemented system of clause 61, wherein the radiation attenuation by the second structure with respect to time represents an indicator of vascular perfusion of the second structure.

63. The computer-implemented system of clause 55, wherein the scanning-frequency control module is further configured to decrease the frequency below the third rate in response to detection of a decrease in a rate at which the attenuation is decreasing.

64. The computer-implemented system of clause 63, wherein the scanning-frequency control module is further configured to decrease the frequency further below the third rate with each successive scan.

65. The computer-implemented system of clause 64, wherein the scanning-frequency control module is further configured to divide the frequency by approximately two with each successive scan.

66. The computer-implemented system of clause 55, wherein the scanning-frequency control module is further configured to reduce the frequency to the third rate upon a first detection of a decrease in attenuation after an increase to the second rate.

67. The computer-implemented system of clause 55, further comprising a termination module configured to terminate the scanning after a predetermined period of time and direct performance of a final scan at the end of the predetermined period.

68. The computer-implemented system of clause 55, further comprising a termination module configured to terminate the scanning after a predetermined period of time, and, if a remaining time between a latest scan and an end of the predetermined period is less than an interval between the latest scan and an immediately preceding scan, direct performance of (i) a penultimate scan at a half of the remaining time after the latest scan and (ii) a final scan at the end of the predetermined period.

69. A computed tomography imaging system, comprising:
a gantry comprising an opening configured to accommodate an object;
a radiation source mounted to the gantry;
a radiation detector mounted to the gantry opposite the radiation source relative to the opening;
an attenuation monitoring module configured to monitor, during an imaging session, an indicator of attenuation of radiation by a contrast-enhanced structure within a target region;
a scanning-frequency control module configured to (i) increase a frequency of scanning from a first rate to a second rate after detection of an increase of the attenuation, and (ii) decrease the frequency to a third rate after detecting a decrease in attenuation after increasing the frequency to the second rate.

70. A method of computed tomography imaging, comprising:
  repeatedly emitting x-ray radiation into a target region at a frequency during a session;
  monitoring, during the session, an indicator of attenuation of radiation by a contrast-enhanced first structure within the target region;
  varying the frequency based on the attenuation.

71. The method of clause 70, wherein x-ray radiation is emitted at a minimum frequency when the attenuation is below a low threshold and at a maximum frequency when then attenuation is above a high threshold.

72. A method of contrast-enhanced computed tomography (CT) imaging, comprising:
  (a) repeatedly scanning a target region during a session, the scanning comprising performing a CT scan by emitting x-ray radiation at an applied power toward the target region, the applied power being a first power for a first scan;
  (b) monitoring an indicator of attenuation of radiation by a contrast-enhanced first structure within the target region; and
  (c) selecting the applied power for each of a plurality of scans, after a first scan, based on the attenuation indicated from a preceding scan in the session.

73. The method of clause 72, wherein the first power is a maximum power applied during the session.

74. The method of clause 72, wherein the applied power is determined by selection of an applied current.

75. The method of clause 74, wherein the first applied current is about 200 ma.

76. The method of clause 72, further comprising applying substantially the first applied power to individual scans until detection of an increase of the attenuation to or beyond a threshold attenuation magnitude.

77. The method of clause 76, wherein the threshold attenuation magnitude is about 35 HU.

78. The method of clause 76, wherein the threshold attenuation magnitude is a predetermined proportion of the attenuation determined from an initial scan.

79. The method of clause 76, wherein the threshold attenuation magnitude is a predetermined number of Hounsfield Units greater than the attenuation determined from an initial scan.

80. The method of clause 72, wherein the applied power is selected by multiplying a maximum current by an exponential function based on the attenuation determined from the preceding scan.

81. The method of clause 80, wherein the exponential function yields a value that is (i) greater than a minimum allowable current divided by a maximum allowable current, and (ii) less than 1.

82. The method of clause 80, wherein the exponential function is a function F determined by $$F = e^{C \cdot (TH - \Delta HU)/TH}$$

wherein TH is a threshold attenuation magnitude and $\Delta HU$ is equal to a difference in magnitude, in Hounsfield Units, between the attenuation determined from a preceding scan and a baseline attenuation.

83. The method of clause 82, wherein the preceding scan is a scan immediately prior to a scan performed according the applied power as determined by the function F.

84. The method of clause 82, wherein the baseline attenuation is a magnitude of the attenuation indicated based on the initial scan.

85. The method of clause 82, wherein C is selected such that, when the function is applied, an applied current for a next scan is about a tenth of the maximum allowable current when the attenuation of the preceding scan is about ten times above the threshold attenuation magnitude.

86. The method of clause 82, wherein C is about 0.25.

87. The method of clause 82, further comprising selecting an applied power corresponding to a minimum allowable current for each scan for which the function F indicates, based on the attenuation indicated by a preceding scan, a current less than the minimum allowable current.

88. A computer-implemented system for controlling contrast-enhanced computed tomography imaging, comprising:
  an attenuation monitoring module configured to monitor, during an imaging session, an indicator of attenuation of radiation by a contrast-enhanced structure within a target region;
  a power control module configured to select an applied power for each of a plurality of scans based on the attenuation detected from a preceding scan.

89. The computer-implemented system of clause 88, wherein the power control module is further configured to direct application of a maximum power applied during the session in a first scan.

90. The computer-implemented system of clause 88, wherein the power control module is further configured to apply substantially the same amount of power to individual scans until detection of an increase of the attenuation to or beyond a threshold attenuation magnitude.

91. The computer-implemented system of clause 88, wherein the power control module is further configured to select the applied power by multiplying a maximum current by an exponential function.

92. A computed tomography imaging system, comprising:
  a gantry comprising an opening configured to accommodate an object;
  a radiation source mounted to the gantry;
  a radiation detector mounted to the gantry opposite the radiation source relative to the opening;
  an attenuation monitoring module configured to monitor, during an imaging session, an indicator of attenuation of radiation by a contrast-enhanced structure within a target region;
  a power control module configured to select an applied power for each of a plurality of scans based on the attenuation detected from a preceding scan.

93. A method of computed tomography imaging, comprising:
  repeatedly emitting x-ray radiation into a target region, each emission having an input power;
  monitoring an attenuation of radiation through a structure within the target region;
  varying the input power based on the attenuation.

94. The method of clause 93, further comprising applying a minimum input power when the attenuation is above a high threshold and applying a maximum input power when then attenuation is below a low threshold.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 11 and 12 are schematic diagrams of dynamic axial collimator leaves.

FIGS. 13-15 are plots of the velocities (in cm/s) for a transverse collimator leaf.

DETAILED DESCRIPTION

Figure 1:
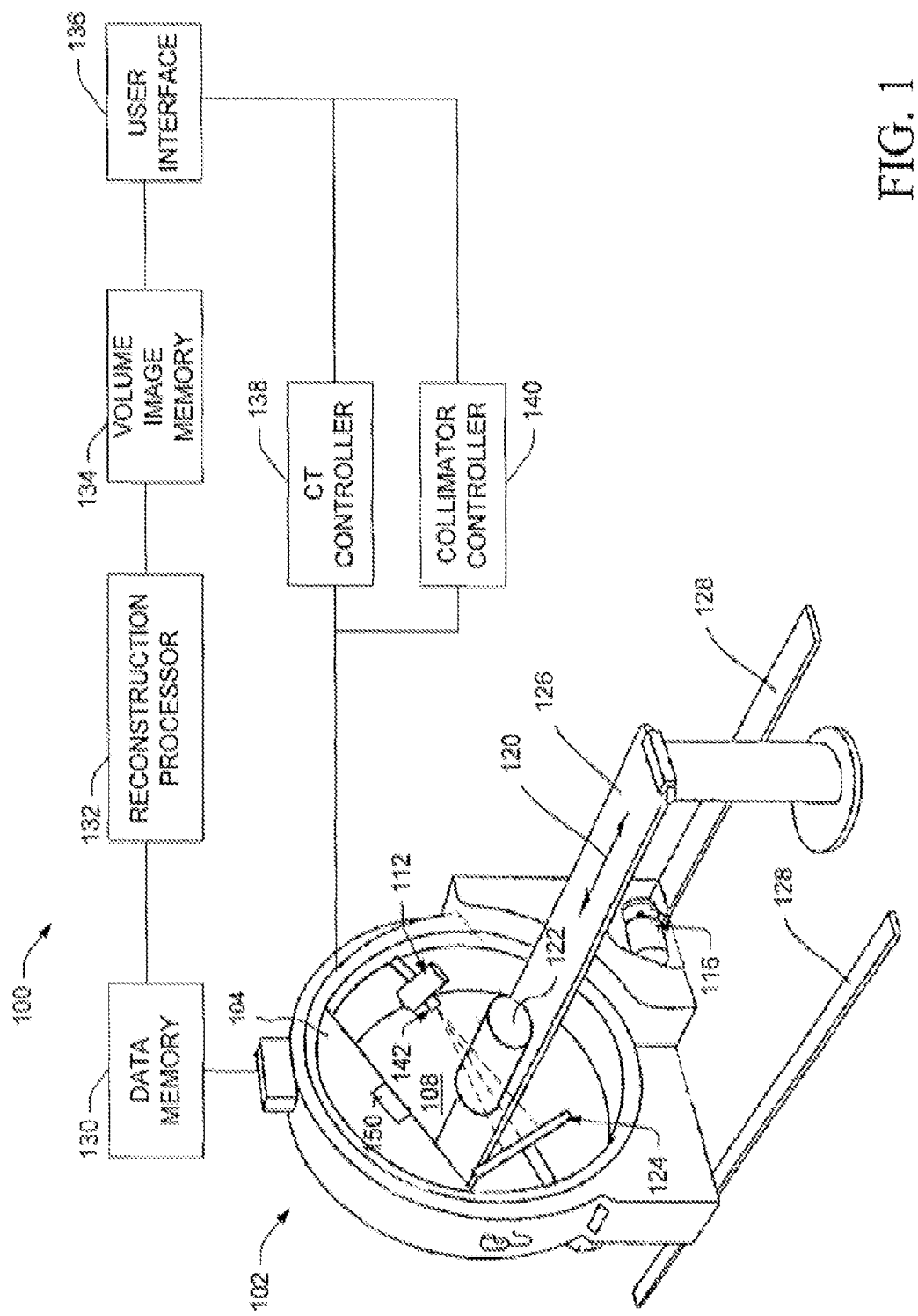
FIG. 1 illustrates an exemplifying CT imaging system according to an embodiment.
Figure 2:
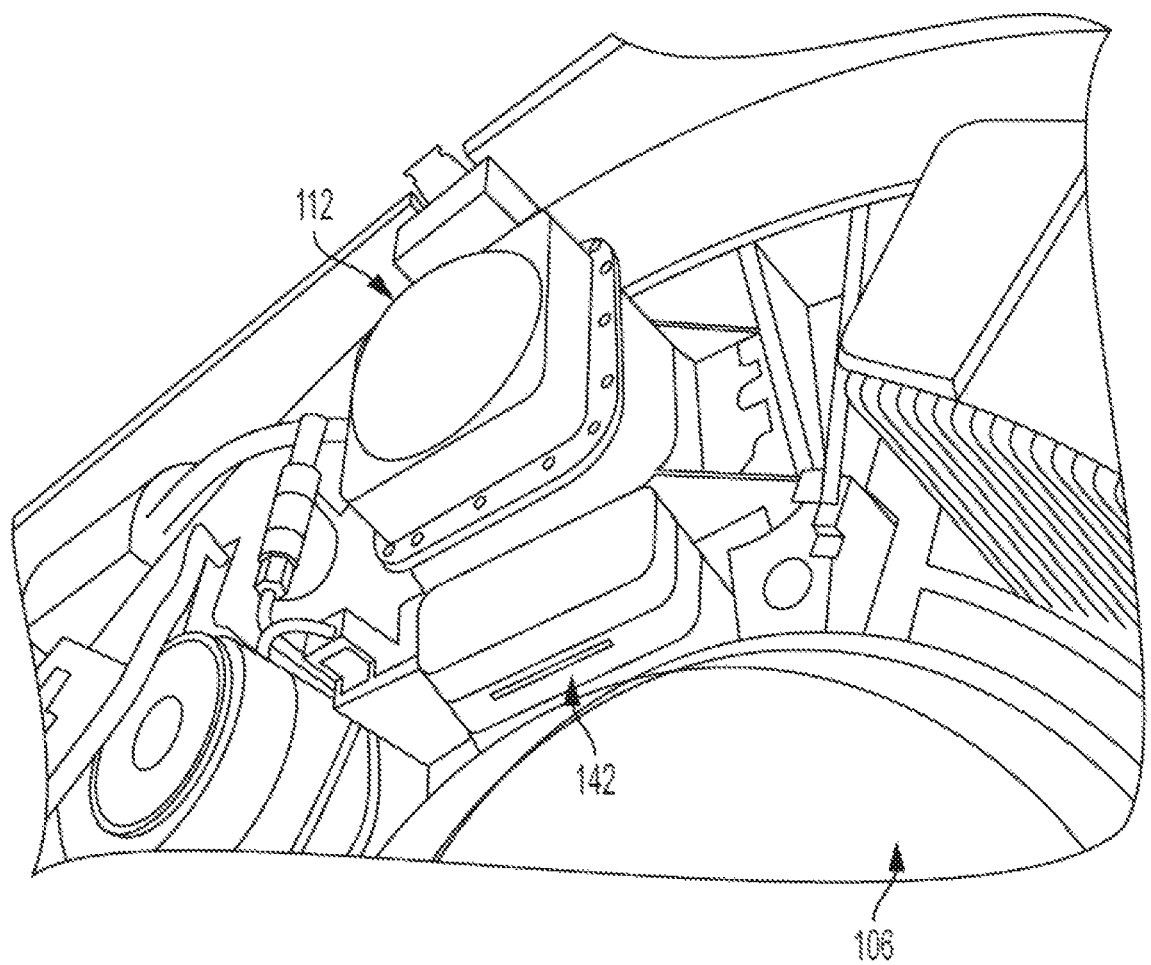
FIG. 2 is an enlarged perspective view of a radiation source mounted to a rotatable gantry and a transverse collimator positioned along a path of radiation emission.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Although many features, aspects and embodiments are described herein or shown in the accompanying drawings in the context of CT, the disclosed technology can also be applied in other imaging systems and methods, other medical scenarios, or other image data acquisition or processing techniques.

Primarily due to concerns about the magnitude of radiation dose delivered, perfusion CT imaging has not been used routinely in various fields, including stroke assessment, oncology, and cardiac and kidney function. In some embodiments, reduction of radiation dose delivered to a subject can permit application of perfusion CT to those applications wherein dose is a limiting factor, e.g. cardiac perfusion. In some embodiments, perfusion CT can be applied to stroke assessment, oncology, and assessment of cardiac and kidney function. In various embodiments, a radiation dose delivered to a subject can be reduced by application of a transverse dynamic collimator, a grated collimator, an adaptive sampling algorithm, an adaptive exposure algorithm, or a combination thereof. In some embodiments, the radiation dose of perfusion CT can be significantly reduced without impacting diagnostic accuracy During a helical CT scan, an X-ray source generates a cone (or wedge) beam of radiation that moves relative to the patient. Portions of the cone beam of radiation may not pass through the volume to be reconstructed. While this extra radiation may have little adverse effect on the clinical use of the reconstructed image, it can subject the patient to more radiation than is necessary. Accordingly, various embodiments described herein relate to replacing a conventional collimator with a dynamically transversely adjustable collimator. The collimator can be actuated by an electromechanical servo system. The imaging system can comprise a control (e.g., an electronic control) that is responsive to sensor(s) for sensing the axial and rotational position of the X-ray source relative to a volume of interest. As the X-ray source rotates about an axis, the collimator is adjusted (i) to adjust the width, location, or both of the radiation beam so that radiation is primarily allowed to pass through the volume of interest and (ii) to block some or all of the rays of radiation that will not intersect the volume of interest.

FIG. 1 illustrates an exemplifying CT imaging system 100 including a CT scanner 102 with a gantry portion 104, a radiation source unit 112, a detector 124, and a couch or support 126. The gantry portion 104 can comprise a gantry opening 106 and can rotate about an examination region 108. The rotating gantry portion 104 can support the radiation source unit 112 and the detector 124.

The radiation source unit 112 can be an x-ray source, such as an X-ray tube, for example. The radiation source can emit a radiation beam. The radiation beam can be a cone beam, wedge beam, or other desirable beam shape. The beam can be collimated to have a generally conical geometry in some embodiments.

The detector 124 is sensitive to radiation (e.g., x-ray) emitted by the radiation source unit 112. In some embodiments, the detector 124 can be a detector array comprising multiple radiation detectors. The detector 124 can be disposed opposite the x-ray source unit 112 on rotating gantry portion 104. In some embodiments, the detector 124 includes a multi-slice detector having a plurality of detector elements extending in the axial and transverse directions. Each detector element can detects radiation emitted by the radiation source unit 112 that traverses the examination region 108 and can generate corresponding output signals or projection data indicative of the detected radiation. Other detector configurations, such as those wherein stationary detectors surround the examination region, can also be used.

The motion of the radiation source and emission of radiation thereby are coordinated to scan a volume of interest (VOI) 122 such as anatomy, or a portion of anatomy, disposed within the examination region 108. The volume of interest can be enhanced with a contrast agent in some embodiments, such as described below, for example. In some embodiments, coordinated motion and radiation emission can be used for fly-by scanning, for example. In some embodiments, the radiation source and detector move in coordination with a contrast agent through the subject such that the VOI is scanned in coordination with the flow of the agent as it is traced through the VOI. In another embodiment, the axial advancement is coordinated with a motion of the subject to capture a desired motion state.

The support 126 can support a subject, such as a human patient for example, in which the VOI is defined within the examination region 108. As illustrated in FIG. 1, a drive mechanism 116 can move the radiation source longitudinally along a z-axis 120 on tracks 128 while the support 126 is stationary. In some embodiments, however, the support 126 can be translated axially along the z-axis 120 while the gantry 104 rotates in a fixed location along the z-axis. An operator of the system can define the VOI to encompass the whole subject or a portion thereof for scanning. In one embodiment, the CT scanner performs a helical scan of the VOI by rotating around the axis 120 during relative movement of the gantry and the support parallel to the axis.

The system 100 can further comprise various computer hardware and software modules. As illustrated in FIG. 1, for example, the system can comprise data memory 130, a processor 132, a volume image memory 134, a user interface 136, and one or more controllers, such as a CT controller 128 and a collimator controller 140. In some embodiments, a single hardware or software module can control multiple parts of the system 110, such as the radiation source and one or more collimators, for example.

The projection data generated by the detector 124 can be stored to a data memory 130 and reconstructed by a processor 132 to generate a volumetric image representation therefrom. The reconstructed image data can stored in a volume image memory 134 and displayed to a user via a user interface 136. Although FIG. 1 separately illustrates the data memory 130 and the volume image memory 134, both can be stored within common data storage hardware. The image data can be processed to generate one or more images of the scanned region or volume of interest or a subset thereof.

The user interface 136 facilitates user interaction with the scanner 102 and can comprise various input and output devices.

Software applications and modules can receive inputs from the user interface 136 to configure and/or control operation of the scanner 102, and other elements of the system 100. For instance, the user can interact with the user interface 136 to select scan protocols, and initiate, pause, and terminate scanning. The user interface 136 can display images, facilitate manipulation of the data and images and measurement of various characteristics of the data and images, etc.

An optional physiological monitor (not shown) can monitor cardiac, respiratory, or other motion of the VOI. For example, the monitor can include an electrocardiogram (ECG) or other device that monitors the electrical activity of the heart. This information can be used to trigger one or more scans or to synchronize scanning with the heart electrical activity to reduce or eliminate adverse affects of heart motion on imaging. An optional injector (not shown) or the like can be used to introduce agents, such as contrast for example, into the subject. Introduction of the agent can be used to trigger one or more scans.

The CT controller 138 can control rotational and axial movement of the radiation source unit 112 and the detector 124 relative to the support 126. The CT scanner and CT controller can be coupled to a collimator controller 140 that controls a collimator 142 positioned between the radiation source and the examination region 108. Although FIG. 1 illustrates the CT controller and the collimator controller as separate units, the CT scanner and one or more collimators can be controlled by the same hardware and software modules in some embodiments.

The collimator controller 140 can control movement, and opening and closing, of a radiation delivery window of the collimator 142. In some embodiments, the collimator controller can independently control movement of individual leaves of the collimator. The collimator controller can be a software module configured to move leaves of a collimator to allow passage of radiation toward a region of interest while blocking radiation to portions of a subject outside the region of interest.

In some embodiments, the collimator controller 140 can cause the collimator to function as a shutter to block radiation between scans and to open, close, and translate as the rotatable gantry 104 (and accordingly the source unit 112 and detector 124 coupled thereto) move around the VOI 122 during a scan.

In some embodiments, the collimator controller 140 can include one or more electromechanical servo motors. In some embodiments, the collimator controller 140 can include an electronic controller.

Collimation

Figure 3:
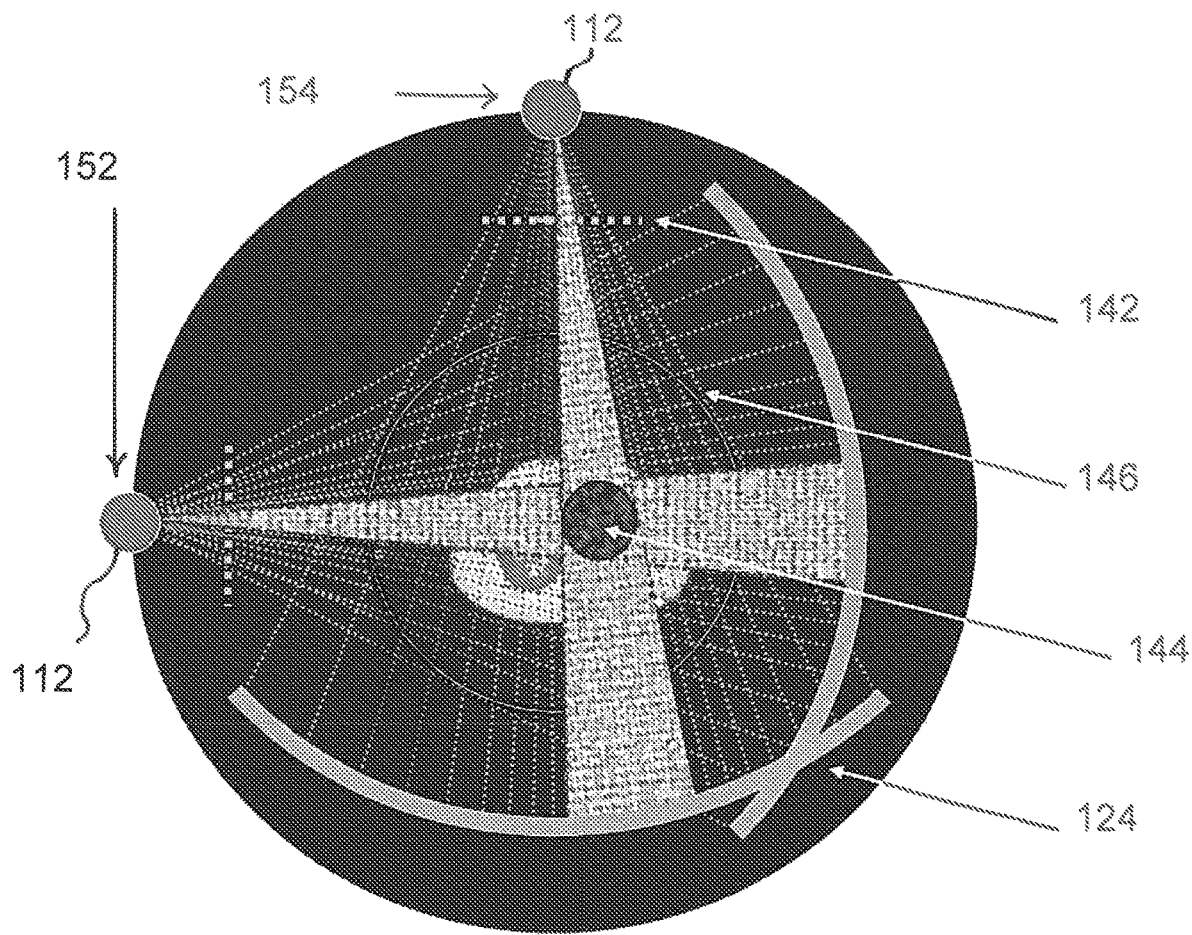
FIG. 3 illustrates limitation of radiation exposure to a region of interest at multiple positions of a dynamic transverse collimator according to an embodiment.
Figure 4:
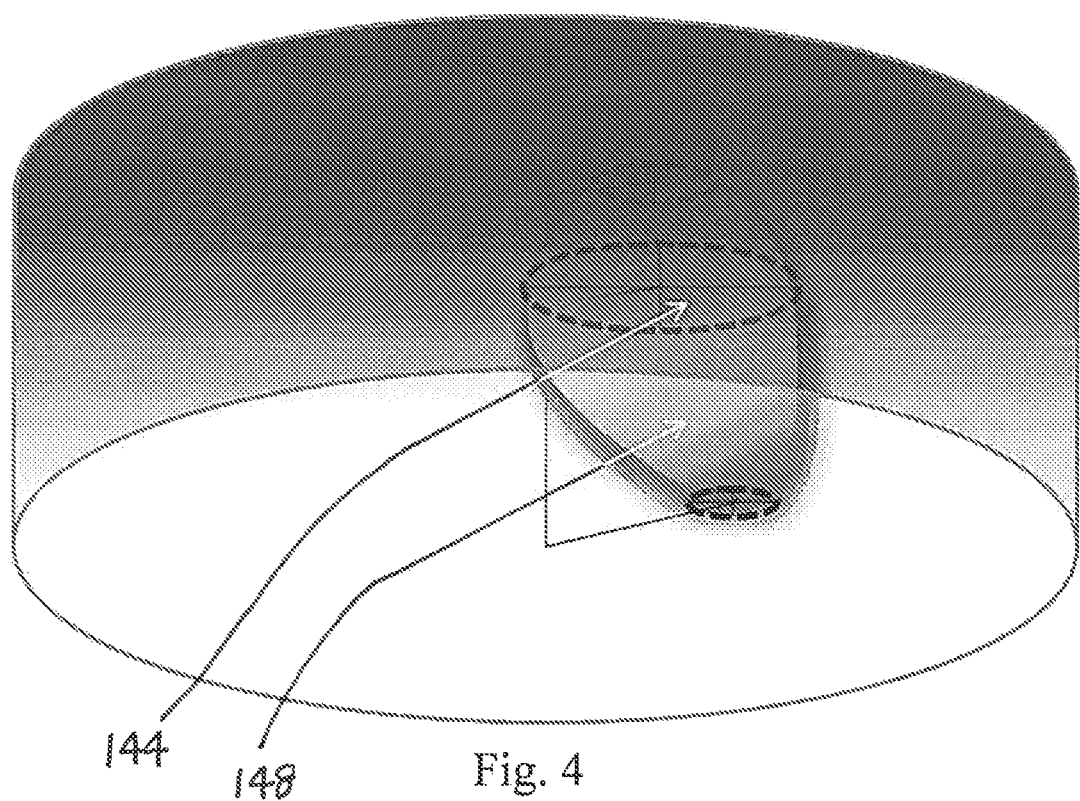
FIG. 4 illustrates the outline of volume of interest (VOI) corresponding to a heart.

Repeated large area circular scans and helical scans can be used to perform perfusion CT. By opening, closing, and/or translating the collimator 142, radiation can be delivered primarily only along paths that intersect the VOI, thereby reducing the X-ray dose. In the case of helical scans, a dynamic axial collimator can be used to limit the x-ray exposure, axially, at either end or both ends of the helical scan. For example, in some embodiments, an axial collimator can be gradually opened at the leading end of the VOI and closed at the trailing end of the VOI. A dynamic transverse collimator positioned in a plane transverse to a gantry rotation axis and in front of the x-ray source can limit the x-ray exposure to a region of interest (ROI) 144 within a field of view (FOV) 146, as illustrated in FIG. 3. FIG. 3 is a schematic illustration of an imaging system showing two positions 152, 154, respectively at 0 and 90 degrees relative to a subject, of the radiation source unit 112, detector 124, and a dynamic transverse collimator 142 for an off-center ROI 144 surrounding the heart. FIG. 4 illustrates the outline of a VOI corresponding to the heart. Transverse and axial collimators can together limit the x-ray exposure to primarily only the VOI 148 for the heart illustrated in FIG. 4, for example. As illustrated, for example, in FIG. 4, the VOI 148 can include multiple ROIs 144.

Figure 5:
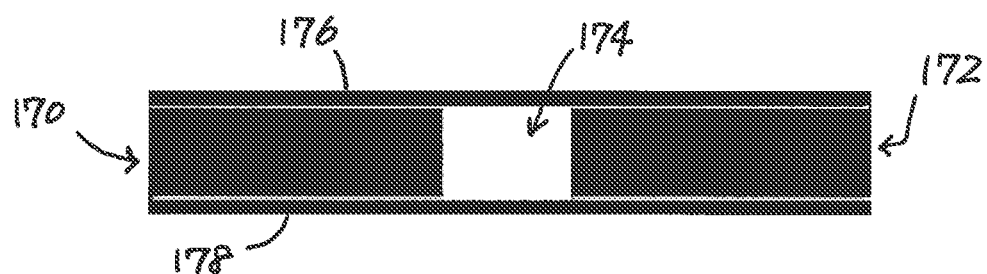
FIG. 5 schematically illustrates an exemplifying embodiment of a dynamic collimator according to an embodiment.
Figure 7:
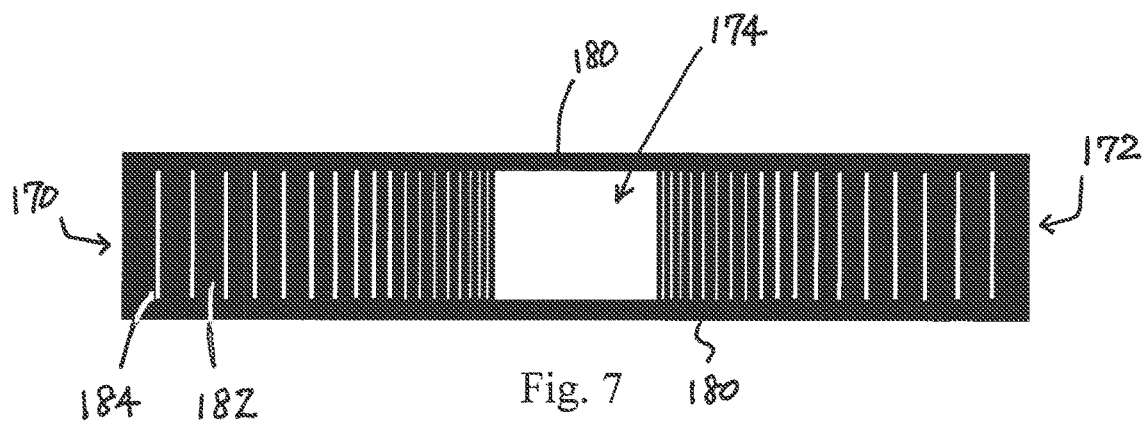
FIG. 7 illustrates an exemplifying embodiment of a dynamic grated collimator according to an embodiment.

In some embodiments, a collimator can comprise a first leaf 170 and a second leaf 172 respectively bounding first and second opposing sides of a radiation delivery window 174, as illustrated in FIG. 5, for example. The first leaf and the second leaf can be movable to adjust at least one of a size or a location of the radiation delivery window relative to the radiation source in a direction non-parallel to the axis. The first leaf and the second leaf can be independently movable relative to the radiation source in a direction non-parallel to the axis. The first leaf 170 and the second leaf 172 can be moveable independently of each other. Each of the first and second sides can be substantially orthogonal to each of the third and fourth sides opposing sides of the radiation delivery window 174. In some embodiments, the first leaf and the second leaf can be independently movable relative to the radiation source in a direction tangential to a circle (i) centered on the axis and (i) defining a plane that is not parallel to the axis. In some embodiments, the leaves can be movable along guide rails 180, as illustrated in FIG. 7.

In some embodiments, the collimator can comprise a third leaf 176 and fourth leaf 178 respectively bounding the third and fourth opposing sides of the window. The third leaf, the fourth leaf, and the window can be arranged generally along a line that is parallel to the axis of gantry rotation. The window can be interposed between the third and fourth leaves such that radiation is transmitted between the third and fourth leaves in a direction generally perpendicular to the axis of rotation. The third leaf and the fourth leaf can be independently movable relative to the radiation source with a direction of motion being generally parallel to the axis. The third leaf 176 and the fourth leaf 178 can be moveable independently of each other. In some embodiments, the third and fourth leaves can be movable independently of the first and second leaves.

The transverse and axial collimators can be driven by the same motor or different motors. Similarly, the transverse and axial collimators can be controlled by the same hardware or software modules. In some embodiments, transverse and axial collimators can be integrated into a single unit.

The VOI can be defined, for example, by a previously-acquired very low dose scan of the same region or two orthogonal localizer scans could be used. An operator can specify an axial extent of the VOI and the size, shape, and location of each ROI along the axial direction. In some embodiments, an outline of the entire VOI can be drawn from two orthogonal views, e.g. sagittal and coronal views, with the images zoomed according to the largest ROI in the sequence. The truncated region of each reconstructed image can be displayed with a dark background.

The axial collimator leaves can be opened and closed based on the axial extent of the VOI. If the VOI is modeled using elliptical cross-sections, the transverse collimator leaves can move smoothly as they closely follow the outline of the VOI. In the case of a large cone-beam, the beam already encompasses a large portion of the VOI, therefore there can be less narrowing of the VOI profile at the ends of the scan.

As in the case of the axial collimator, the position of the dynamic transverse collimator leaves can be based on the couch position. However, in the case of the dynamic transverse collimator, as the couch moves in the axial direction, the rotation angle can be used to determine where the current ROI is situated with respect to the source. Given both the couch position and rotation angle, the leaves can continuously follow the outline of the overall VOI. For example, in the case of the cardiac scan shown in FIG. 4, the collimator leaves can follow the ROIs located along the cardiac volume based on the couch location of the ROI as well as the rotation angle of the x-ray source. The ROI along the cardiac volume can have both a non-circular (e.g., elliptical) shape and a location away from a scan center 150.

In some embodiments, for a sequence of axial or circular scans, one ROI can be determined for each scan in the sequence. For each scan, the rotation angle can be used alone to determine the motion of the collimator leaves, adjusting for an off-center and/or non-circular ROI.

In some embodiments, the size of the radiation delivery window 174 between movable leaves of the transverse collimator can be adjusted prior to a scan and held in a fixed arrangement during the scan. For example, a low dose can be performed to identify a VOI, then a subsequent scan can be performed with an transverse collimator aperture dimension selected for imaging of the VOI while the transverse collimator leaves remain stationary during the scan. In some embodiments, the moveable leaves can comprise secondary windows and attenuating members, as discussed further below.

In some embodiments, the collimator can comprise a primary radiation delivery window 174 of a fixed size. In some embodiments, between scans, a collimator having a window of a first fixed size can be removed from the CT scanner 102 and can be replaced with another collimator having a window of a second fixed size, different than the first fixed size. The collimators with primary radiation delivery windows of a fixed size can comprise secondary windows and attenuating members, discussed further below, in some embodiments.

Figure 8:
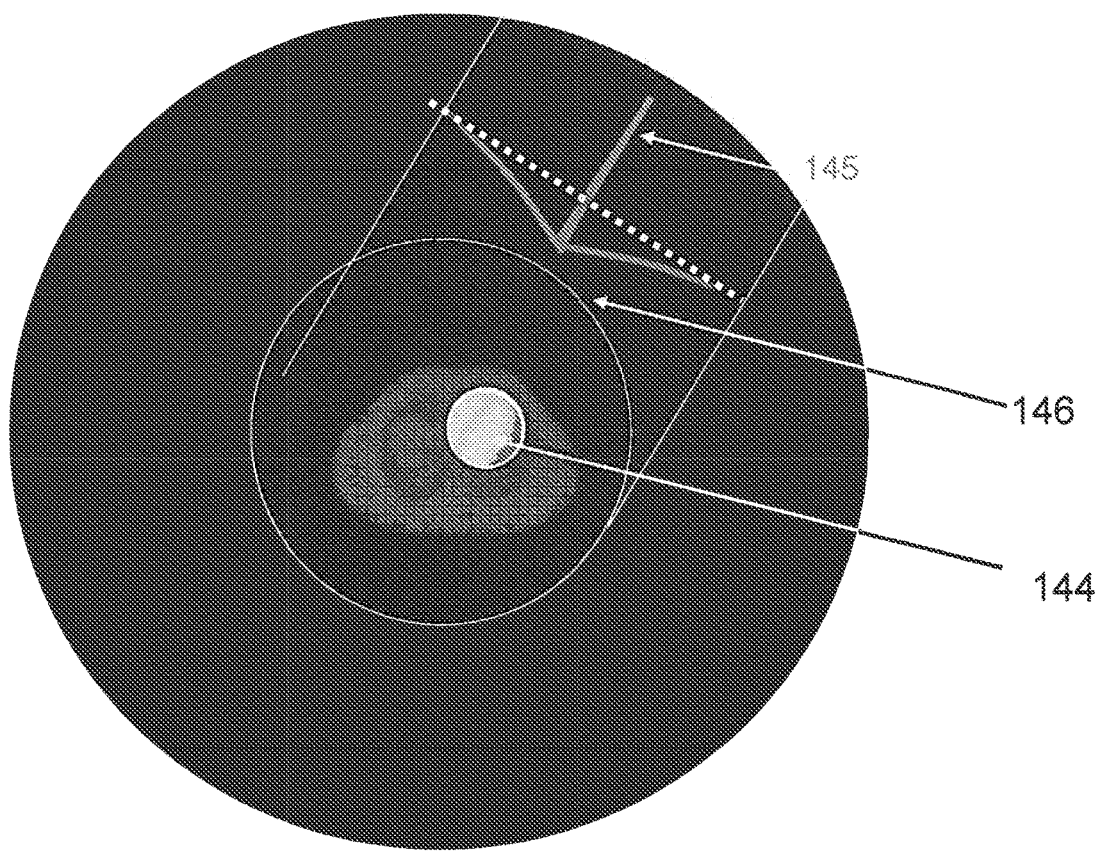
FIG. 8 illustrates a region of interest within a field of view.

As illustrated in FIG. 8, attenuation information from the tissue surrounding the collimated ROI 144 within the FOV 146 is desirable due to the extent of the convolution involved in image reconstruction. Attenuation information 145 for the material outside the collimated VOI can be acquired to facilitate accurate reconstruction. This can be accomplished in various ways, including one or more of the following: (1) use the previously-acquired very low dose scan mentioned above to measure the attenuation outside the VOI; (2) use heavily-attenuated rays through the outer portions of the collimator, providing an estimate of the attenuation outside the VOI so long as the collimator attenuation is previously calibrated; (3) use a projection-completion estimate, extrapolating the truncated projections using a curve-fit based on a simple model; or (4) use limited, but known, attenuation information for isolated sub-regions in the surrounding tissue.

In some embodiments, attenuation values for the region outside the ROI can be determined from radiation passing through windows in a grating that are separated from a primary window configured to allow passage of rays of radiation that would travel through the ROI.

Figure 9:
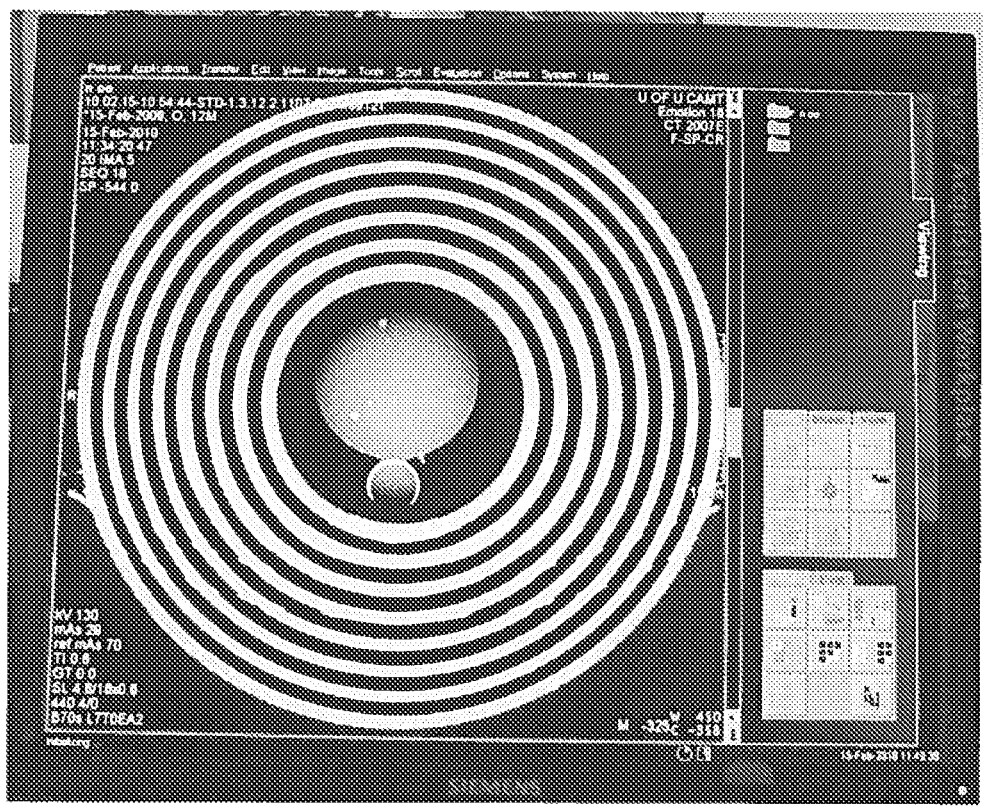
FIG. 9 illustrates an example of an image generated based on a scan using a grated collimator, with no correction applied.

FIG. 9 shows an example of a display output, such as can be displayed on a monitor of a scanner, of a CT scan of an anthropomorphic thorax phantom using a grated collimator. The image of the display output is shown without application of any correction. In some embodiments, correction can be applied to the data used to form the image. In some embodiments, correction can be applied to image data before displaying an image. The VOI in the image of FIG. 9 includes a phantom cardiac region near the center of the thorax phantom.

In some embodiments, the collimator 142 can comprise a first grating 170 and a second grating 172 positioned on opposing sides of a primary radiation delivery window 174. Each of the first and second gratings can comprise a plurality of attenuating members 182 with a plurality of secondary radiation delivery windows 184 extending between adjacent attenuating members of the first grating and the second grating, respectively.

Figure 6:
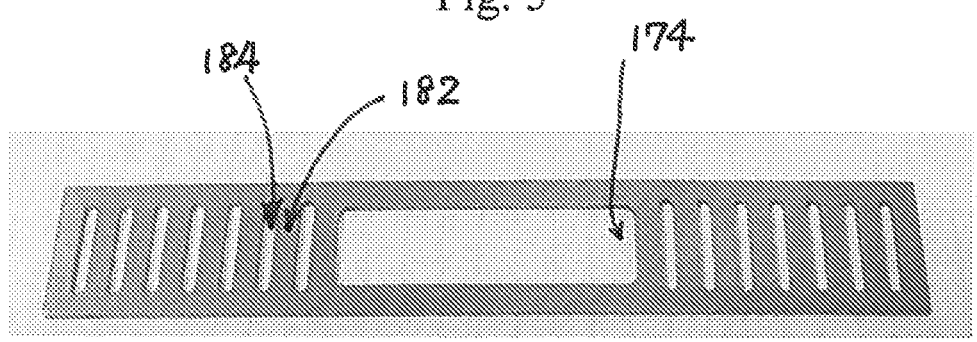
FIG. 6 illustrates a perspective view of an exemplifying embodiment of a grated collimator according to an embodiment.

A width of each secondary window can be less than a width of the primary window, as illustrated in FIG. 6, for example. Although FIG. 6 illustrates attenuating members of the first grating and the second grating as being integral with each other, the first and second gratings can be part of separate first and second leaves 170, 172, as illustrated in FIG. 7, for example. A total area of each of the secondary windows can be less than a total area of the primary window. In some embodiments, the width of each secondary window can be proportional to a distance between the secondary window and the primary window, as illustrated in FIG. 7, for example. For example, the width of each secondary window can be linearly, exponentially, or geometrically proportional to the distance between the secondary window and the primary window. The width of each secondary window can be positively proportional to the distance between the secondary window and the primary window such that the width of the windows increase with their distance from the primary window. The secondary windows can be oriented generally parallel to sides of the primary window. The secondary windows can comprise open passages extending through the grating. In some embodiments, the secondary windows can comprise panes of substantially radio-transmissive or low-attenuating material. When panes of low-attenuating material are employed, the panes can attenuate the radiation to a lesser extent than the attenuating members 182.

A width of each attenuating member, and thus the spacing between secondary windows, can be proportional to a distance between the attenuating member and the primary window, as illustrated in FIG. 7, for example. The width of each attenuating member can be linearly, exponentially, or geometrically proportional to the distance between the attenuating member and the primary window. The width of each attenuating member can be positively proportional to the distance between the attenuating member and the delivery window. The attenuating members can be oriented generally parallel to sides of the primary window. In some embodiments, the attenuating members can block passage of x-ray radiation therethrough. In some embodiments, the attenuating members can be made of materials that substantially prevent transmission of x-rays. The attenuating members can be made of lead, tungsten, or other materials or combinations thereof.

In some embodiments, the size, number, position, spacing, or a combination thereof of the secondary windows and attenuating members can provide approximately a minimum or a near-minimum amount of radiation transmission for detector operation.

Collimator Control

The collimator controller, which can be a hardware or software module, can be configured to control operation of transverse dynamic collimators to significantly reduce the radiation dose delivered by CT scans. In some embodiments, the collimator controller can control both axial and transverse collimators. Further details regarding axial collimators and their control are provided in U.S. Patent Application Publication No. 2010/0246752 to Heuscher et al., entitled Dynamic Collimation in Cone Beam Computed Tomography to Reduce Patient Exposure, the entirety of which is hereby incorporated herein by reference. In some embodiments, a single collimator can be configured for both axial and transverse collimation. A axial collimator and a transverse collimator can be integrated as a single unit in some embodiments. The transverse dynamic collimator, whether alone or in combination with the axial collimator, can be used for both helical and axial scans.

In some embodiments, the leaves of the axial and transverse collimators can be moved such that only or substantially only that radiation, e.g., x-rays, that intersects a predefined VOI is exposed to the patient.

In some embodiments, control of the transverse collimator involves the velocity of each leaf. The velocity of each leaf can be determined for a region of interest (ROI) at a given distance from scan center. In some embodiments, the ROI in a particular slice can be circular or noncircular. The velocity and acceleration of leaf movement depend on how far off-center a given cross-sectional region of interest (ROI) is located from a scan center within a field of view (FOV).

Figure 10:
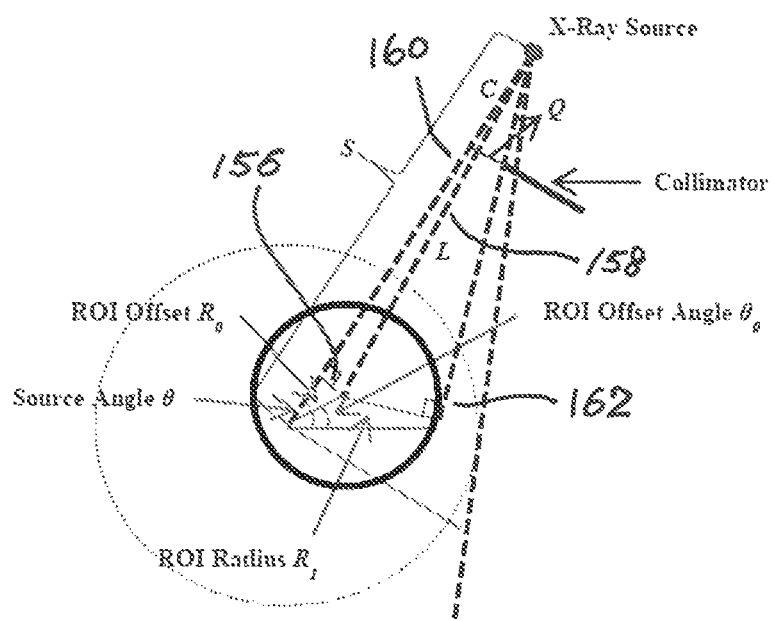
FIG. 10 is a schematic diagram of transverse dynamic collimator geometry according to an embodiment.

Referring to FIG. 10, the following equations can define the transverse collimator leaf position Q(t) and approximated velocity Q' given the rotation speed $\rho$, collimator distance C, distance S from an ideal radiation point source to the scan isocenter, ROI radius $R_1$, and offset $R_0$ at angle $\theta_0$.

$$Q(t) = C \cdot \tan\left(\arcsin\left(\frac{R_1}{L(t)}\right) + \arcsin\left(\frac{R_0}{L(t)} \cdot \sin(\theta(t) - \theta_0)\right)\right) \quad (1)$$

$$L(t) = \sqrt{(S \cdot \sin(\theta(t) - \theta_0))^2 + (S \cdot \cos(\theta(t) - \theta_0) - R_0)^2} \quad (2)$$

$$\frac{\partial Q(t)}{\partial t} \approx Q'(t) = \frac{C \cdot \pi \cdot R_0}{\rho \cdot S} \cdot \frac{\left(\cos(\theta(t) - \theta_0) - \frac{R_1}{S} \cdot \sin(\theta(t) - \theta_0) - \frac{R_0}{S}\right)}{\left(1 - \frac{R_0}{S} \cdot \cos(\theta(t) - \theta_0)\right)^2} \quad (3)$$

L(t) can represent the distance from the ideal radiation point source to the center 156 of the ROI and can be used to obtain the angle between the line 158 of length L and the central ray of the projection (line 160 of length S). This angle can be added to the remaining angle between the line 158 and the line 162 tangent to the ROI. The distance Q(t) of the collimator leaf from the central ray can be obtained by multiplying the tangent of the resulting angle by a total distance C between the collimator 142 and the point source.

The derivative of the expression for Q(t) can be calculated to calculate the velocity Q'. Assuming a constant rotation speed ρ, the expression 2πt/ρ can substituted for θ(t). Due to its complexity, the derivative of this equation, δQ(t)/δt, can be calculated numerically. In some embodiments, approximations can be made to obtain a closed form expression for obtaining the derivative of the equation δQ(t)/δt. By assuming $R_0$ and $R_1$ are relatively small compared to the point source to isocenter distance S, the higher order terms in the Taylor series expansions of both Q(t) and δQ(t)/δt can be eliminated and a good approximation Q'(t) can be obtained as shown in equation (3).

The leaves of the axial collimator can be opened at the beginning of a scan, e.g., a helical scan, and closed at the end such that only that radiation, e.g., x-rays, that intersect the VOI are exposed to the subject, as illustrated in FIGS. 11 and 12 for the right end of the scanned volume, for example. As the beam, e.g., a cone-beam, approaches the cylindrical VOI from the right, the leaves can be closed, shifted to the far left. As the left edge of the beam touches the far edge of the cylinder, the right leaf can begin opening by moving to the right until the center of the beam reaches the edge of the cylinder. The right leaf then can immediately accelerate to a higher velocity to be able to follow the near edge of the cylinder, until the entire beam is exposed. The collimator can remain open as the scan proceeds until the left edge of the beam hits the near edge of the left side of the cylinder, at which point the left collimator leaf can begin closing in reverse order from the previous sequence for the right leaf.

The following equations can define the axial collimator position Q(t) and velocity δQ/δt given the helical pitch P, helical position H(t), rotation speed ρ, detector width w, collimator distance C, point source to isocenter distance S, and cylindrical VOI radius R:

$$H(t) > 0) \; Q(t) = \frac{C \cdot w}{2 \cdot S} \cdot \left(1 + \frac{2 \cdot P \cdot t}{\rho \cdot \left(1 + \frac{R}{S}\right)}\right) \quad \frac{\partial Q(t)}{\partial t} = \frac{C \cdot w \cdot P}{\rho \cdot (S + R)} \quad (4)$$

$$H(t) < 0) \; Q(t) = \frac{C \cdot w}{2 \cdot S} \cdot \left(1 + \frac{2 \cdot P \cdot t}{\rho \cdot \left(1 - \frac{R}{S}\right)}\right) \quad \frac{\partial Q(t)}{\partial t} = \frac{C \cdot w \cdot P}{\rho \cdot (S - R)} \quad (5)$$

From right to left, as the beam, e.g., cone-beam, approaches the cylindrical VOI, the collimator can attenuate all rays outside the far edge of the cylinder (H(t)>0). Once the center of the beam passes the end of the cylinder (H(t)<0), the collimator can attenuate all rays inside the near edge of the cylinder. Consequently, the denominator of the equations correspondingly changes from (S+R) to (S−R) between equations (4) and (5).

FIGS. 13 and 14 are plots of the velocities (in cm/s) for a transverse collimator leaf where $\theta_0$=0, S=70, and ρ=0.3 s/rev. In FIG. 13, C=27, $R_0$=18, and $R_1$=6. In FIG. 14, C=12, $R_0$=6, $R_1$=6. As illustrated in FIG. 13, for a ROI of 12 cm within a 48 cm diameter FOV and an offset $R_0$ of 18 cm, the transverse collimator leaf can achieve a maximum velocity of 198 cm/s. On the other hand, as illustrated in FIG. 14, if the collimator is located 12 cm from the idealized radiation point source and if the subject is positioned such that the ROI is 12 cm closer to the scan center, the collimator leaf reaches a maximum velocity of 24 cm/s for an offset of 6 cm. Therefore, some embodiments include moving the transverse dynamic collimator closer to the radiation point source, moving the subject closer to the scan center, or both.

Figure 15:
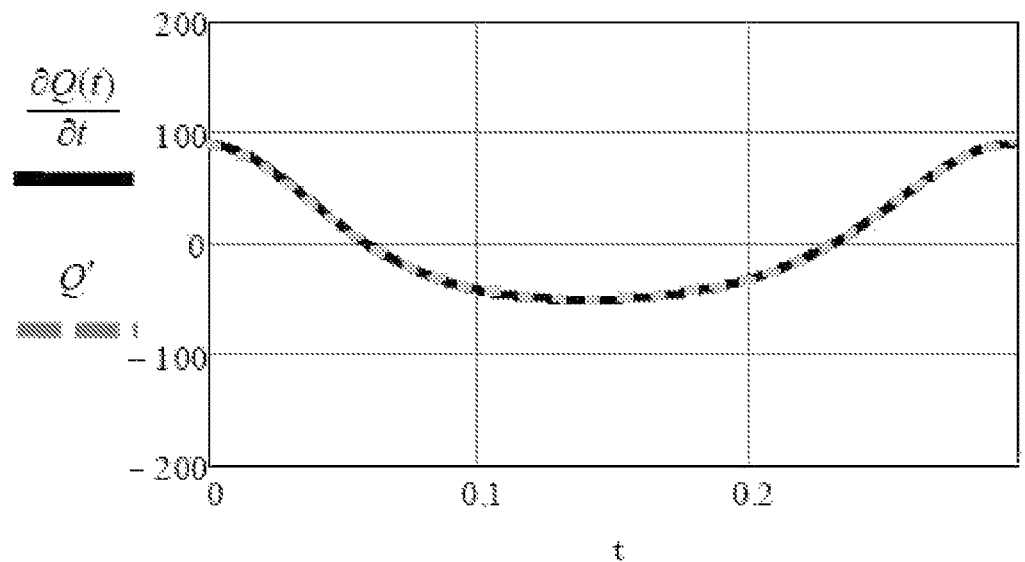

FIG. 15 is a plot of the velocities (in cm/s) for a transverse collimator leaf where $\theta_0$=0, S=70, ρ=0.3 s/rev, C=12, $R_0$=18, and $R_1$=6. Thus, if a velocity of 100 cm/s or less can be tolerated and the collimator is located within 12 cm of the idealized radiation point source, an off-center ROI can be tracked by the collimator and, thus, a subject can remain in the same position within the FOV between a preliminary full-field scan and subsequent scanning targeting to the VOI. FIG. 6 shows that a maximum velocity of 87 cm/s is reached for a 12 cm ROI located 18 cm off-center according to the equations provided herein.

FIGS. 13-15 also compare the closed form approximation Q' (dashed line) with the actual velocity δQ/δt (solid line) computed numerically from Q(t). The close match between the two curves confirms the validity of the approximation for the range of geometric values simulated.

Figure 16:
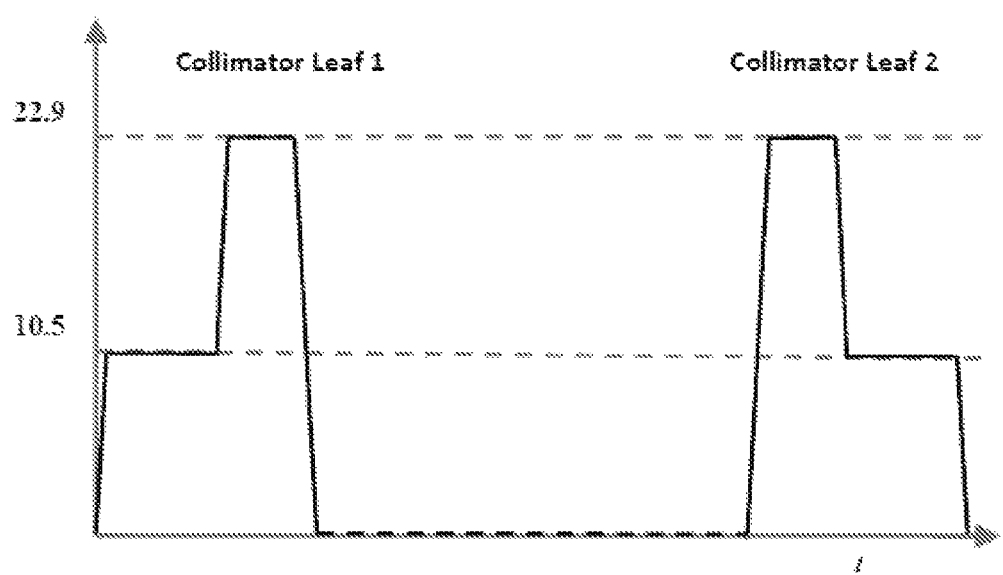
FIG. 16 is a plot of the velocities (in cm/s) for axial collimator leaves.

FIG. 16 is a plot of the velocities (in cm/s) for leaves of an axial collimator where C=27 cm, S=70 cm, a detector width w is 8 cm, a pitch factor P is 1.4, rotation speed ρ is 0.3 sec/rev, and a VOI has a radius R of 25 cm. FIG. 16 shows a maximum axial collimator leaf velocity of 22.9 cm/s. That maximum velocity occurs for H(t)<0, when the center of the cone-beam passes the edge of the cylinder closest to the x-ray source.

The velocity profiles of the transverse collimator leaves and the axial collimator leaves can be compared. The maximum velocity incurred by the axial collimator leaves during a typical helical scan with an 8 cm detector, 0.3 second rotation time (i.e., revolution duration), with a pitch factor of 1.4 is 22.9 cm/sec. On the other hand, the maximum velocity of a transverse collimator positioned 27 cm from the source is 198 cm/sec for a 12 cm cardiac scan located 18 cm from the scan center. Thus, the velocities of the transverse collimator can be greater than the helical collimator. For a transverse collimator mounted 27 cm from the x-ray source, e.g., just beyond the opening of the gantry, the maximum velocity incurred can be more than 8 times that of the axial collimator. However, if the collimator is located closer to the source and if the VOI is positioned, or possibly repositioned, 12 cm or less off-center, the velocities of the transverse and axial collimators can be comparable. In some embodiments, a motor and control system for at least the transverse collimator can provide leaf velocities up to 90 cm/s, patient repositioning can be avoided in more instances. In some embodiments, a motor and control system for at least the transverse collimator can provide leaf velocities greater than 90 cm/s.

Although movement of leaves in a transverse dynamic collimator have been discussed in connection with placement at 12 cm and 27 cm from the radiation source, a transverse dynamic collimator can be positioned at other distances from the radiation source. For example, the transverse dynamic collimator can be positioned within about 27 cm, about 20 cm, about 15 cm, or about 10 cm of the radiation source in some embodiments. In some embodiments, the collimator can be integrated into the radiation source unit 112. By integrating a transverse dynamic collimator into the radiation source unit 112, the distance from the radiation source (measured from the idealized point source location) can be shorter and, thereby, reduce the dynamic requirements (velocity and acceleration) of the transversely moving leaves. However, the distance between the idealized point source and the transverse dynamic collimator is preferably sufficiently long that the size of the radiation penumbra is acceptable. For example, in embodiments that comprise a grated collimator, the distance between the idealized point source and the transverse dynamic collimator is preferably sufficiently long to avoid crosstalk between adjacent secondary windows, e.g., slots, in the grated collimator.

Dynamic Transverse Collimation Dose Reduction

Modeling of heart and kidney scans, with and without transverse dynamic collimation, indicate significant skin dose reduction in both cases. Elliptical models were analyzed to determine the skin exposure for heart and kidney scans. A dose of radiation, e.g., X-rays, exposed to the subject, e.g., a patient, can be significantly reduced using a dynamic transverse collimator such as that illustrated in FIG. 5, for example. The use of other dynamic transverse collimators, such as the grated dynamic transverse collimator illustrated in FIG. 7, can also significantly reduce radiation dose.

Figure 17:
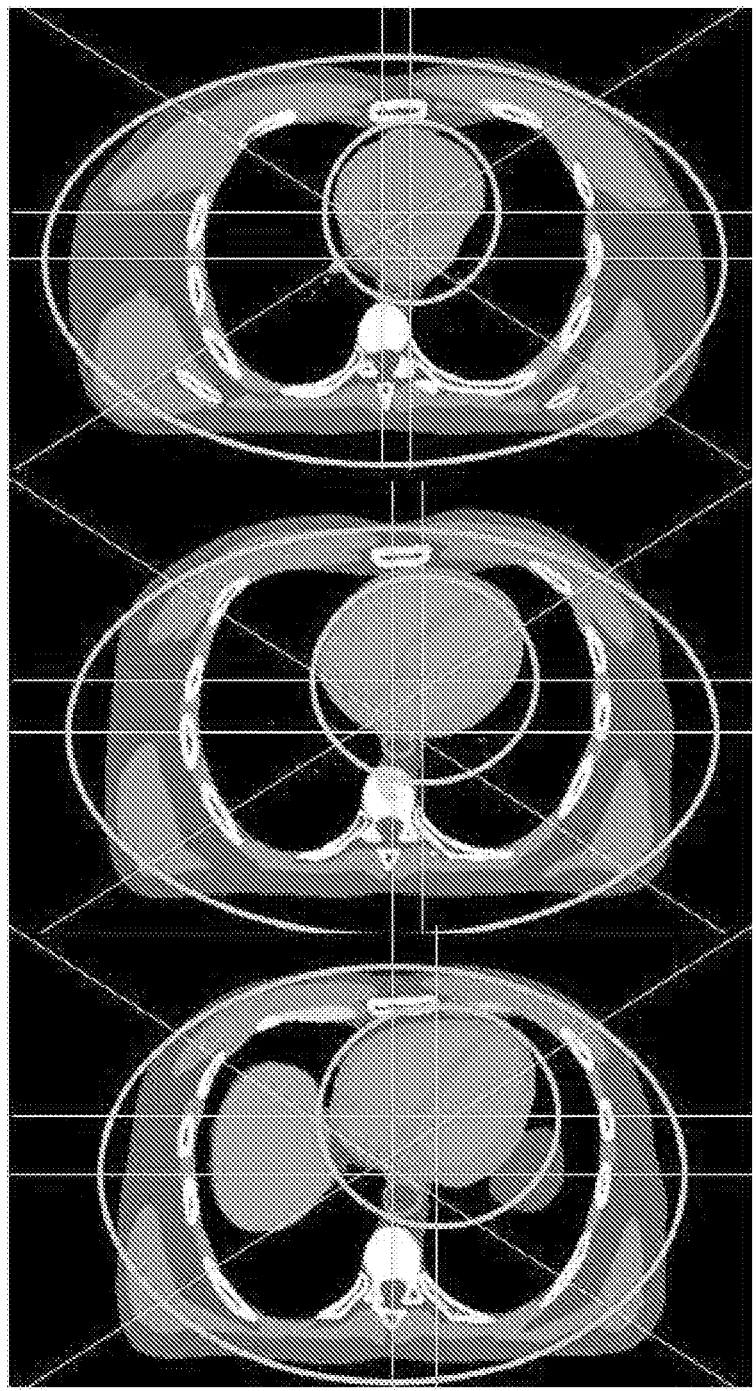
FIG. 17 shows the three cross-sections of a subject, each with an indicated target region of interest.

FIG. 17 shows three cross-sections from the middle of a five cross-section sequence. A target ROI corresponding to a heart is represented by an ellipse in each cross-section of FIG. 17. Dynamic transverse collimation can follows the ellipses outlining the heart and representing the target ROI. The cross-sections of FIG. 17 also include body outlines, approximated with ellipses, from which the skin exposure values were calculated. The five sections of the heart were equally spaced. In the un-collimated case, all sections are fully exposed, while in the collimated case, the exposure is limited to the target VOI, with the first and last sections fully collimated down to a 0 cm diameter circle. Reference lines are shown in FIG. 17 that intersect the scan center, the body ellipse, and target ROI.

The average un-collimated skin exposure relative to the average exposure at the center of the target ROIs is compared to the average collimated skin exposure over the five slices again relative to the average exposure at the center of the target ROI. For the exposure analysis of the heart, reconstructions of an XCAT phantom were used with an X-ray source radius S of 57 cm. A compensator in front of the X-ray source can provide a more uniform signal to the detector and can reduce the overall dose to the patient. Therefore a compensator was modeled that compensates for a disc with a radius rc of 24 cm and an attenuation coefficient equal to water (0.183/cm at 80 KeV, approximately the average energy for a typical CT system performing 120 KeV scans).

As an initial approximation, the water attenuation value of 0.183/cm was assumed for all path lengths throughout the body. The exposure for each of 100 points equally spaced in angle β on the surface of the body ellipse was calculated for 1000 angular views, θ, of the source covering 360 degrees. Rays emanating from the source pass either just through the compensator (FIG. 4), or both through the compensator and the body (FIG. 5). These exposure values were averaged over the 1000 views. The exposure at the center of the target ROI (FIG. 6), was averaged over 1000 views. This provided a reference for the skin exposure values. Thus, all overall skin exposure values were measured as a ratio with respect to the exposure at the center of the target ROI.

For the scans utilizing a dynamic collimator, the fan angles for which the collimated x-rays intersect tangentially to the target ROI were calculated for each x-ray source position and used to exclude all exposure from the x-ray source that fell outside the corresponding angular range. Again, all skin exposure values were averaged over 1000 views.

In the case of the heart, 5 equally-spaced sections of the heart were used to define the cardiac VOI, with the first and last sections fully collimated. The relative skin dose for the center section was compared with and without dynamic collimation. The final skin exposure values were averaged over the five sections, both with and without dynamic collimation.

The boundaries of the ellipses were defined by specifying 6 user-defined points around the periphery of both the body outline and target ROI. A least-squares solution to the parameters of each ellipse, (a, b, r0, t0, tr)=(major axis, minor axis, polar radius of the origin of the ellipse, polar angle of the origin, and angular orientation of the ellipse), was then obtained given the (R,T) polar coordinates of these 6 points along with the following constraints:

$$\frac{X^2}{a} + \frac{Y^2}{b} = 1$$

and $$\left| tr - \frac{\pi}{2} \right| < \frac{\pi}{2}$$

where:

$$X = R \cdot \cos(T-tr) - r_0 \cdot \cos(t_0-tr)$$

$$Y = R \cdot \sin(T-tr) - r_0 \cdot \sin(t_0-tr)$$

(R,T) correspond to the polar coordinates of the 6 points and the following initial values are provided:
(a, b, r0, t0, tr)=(TOL, TOL, com(R,T), mean(T), TOL)
where:

$$com(R,T) = \sqrt{mean(R \cdot \cos(T))^2 + mean(R \cdot \sin(T))^2}$$

TOL=tolerance value=0.00001.

Figure 18:
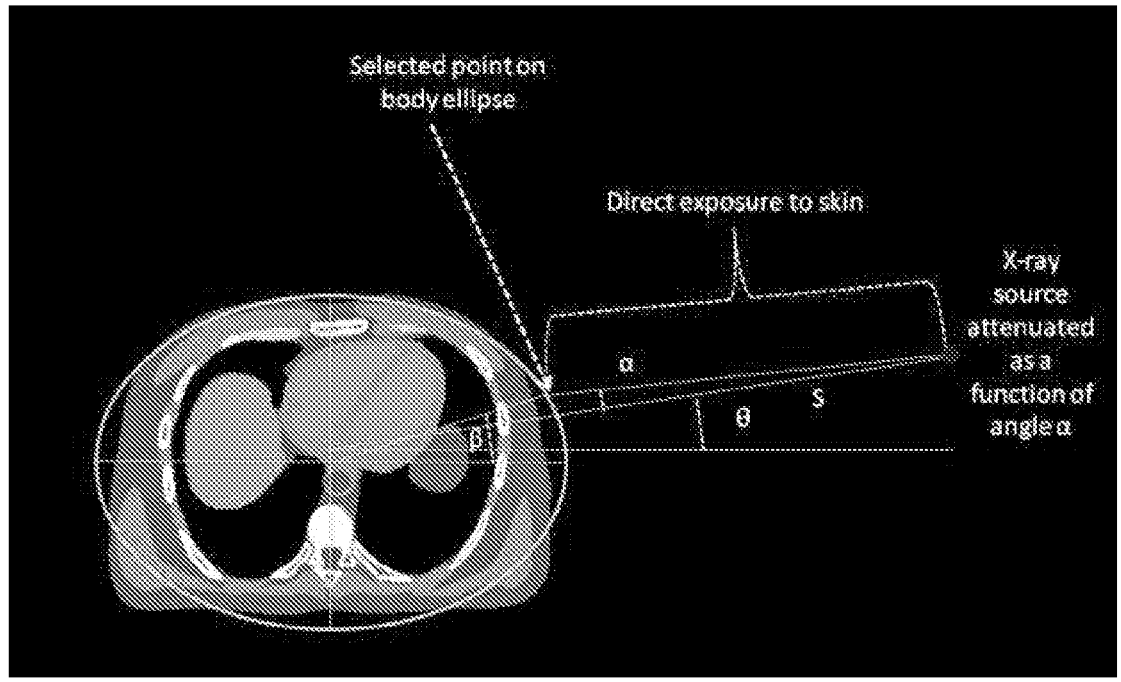
FIG. 18 illustrates geometry for a ray at angle α directly exposing the skin, emanating from the x-ray source located at angle θ.

Given both the body and target ellipses along with the compensator attenuation as a function of the fan angle, the skin exposures was calculated. For all ray angles up to the tangent to the body ellipse, the exposure was the attenuated exposure through the compensator (FIG. 18). For all other angles for which the rays pass through the body to the selected point on the ellipse, the x-ray exposure is further attenuated by the path length through the body. Given the source radius, source angle, and point on the body ellipse, the path length p relative to the distance p0 (FIG. 19) can be calculated as a solution to a quadratic equation resulting from the condition that the entrance point of the ray also satisfies the equation for the body ellipse.

A point on the skin was treated like any other point within the body ellipse. In the case of a point on the boundary of the ellipse directly exposed by the x-ray source, the path lengths through the body converge to zero at all angles up to those angles tangent to ellipse.

FIG. 18 illustrates geometry for a ray at angle α directly exposing the skin, emanating from the x-ray source located at angle θ. The ray illustrated in FIG. 18 is only attenuated by the compensator as a function of angle α.

Figure 19:
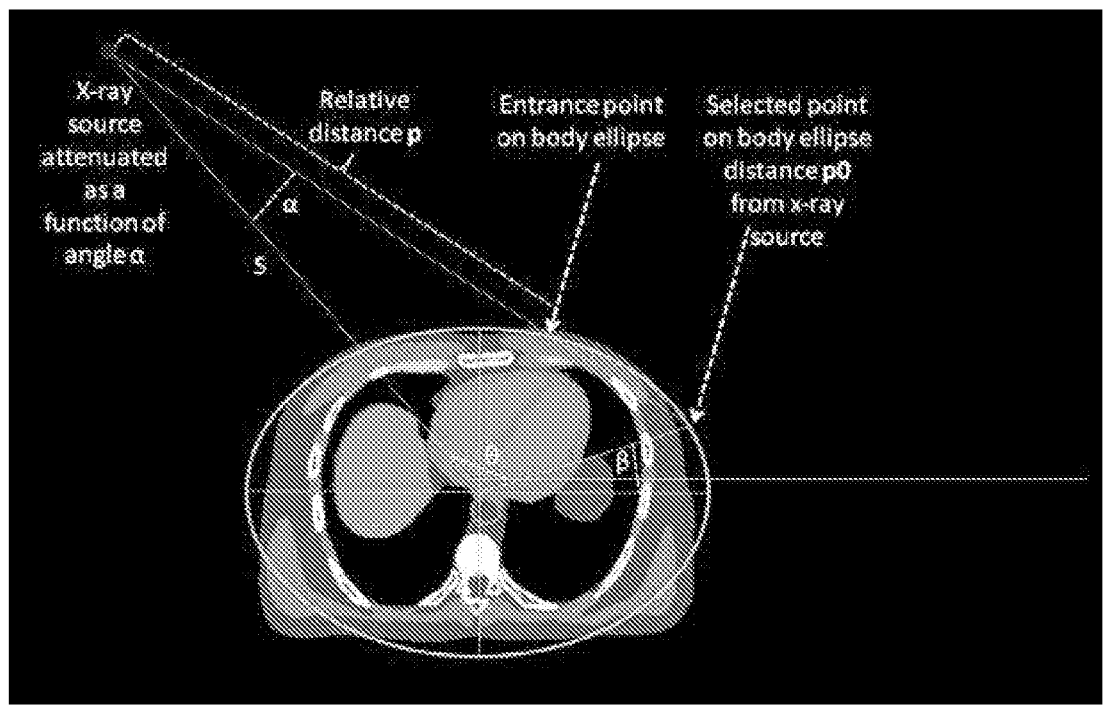
FIG. 19 illustrates another geometry for a ray at angle α indirectly exposing the skin, emanating from the x-ray source located at angle θ.

FIG. 19 illustrates another geometry for a ray at angle α indirectly exposing the skin, emanating from the x-ray source located at angle θ. The ray illustrated in FIG. 19 is further attenuated by the body path length $(1-p) \cdot p0$.

The resulting skin exposure is then calculated as an average value over 360 degrees of the angular position (θ) of the x-ray source:

$$\text{Exposure}(\beta) = .001 \cdot \sum_{i=1}^{1000} (\text{intensity}(\alpha(\beta, \theta_i))) \cdot att(\beta, \theta_i)$$

where:
β=the angle of the point on the body ellipse
θ=the source angle
α=fan angle of the ray intersecting the point on the body ellipse $$\text{intensity}(\alpha) = e^{2 \cdot 0.183 \cdot \left( \sqrt{rc^2 - (S \cdot \sin\alpha)^2} - rc \right)}$$

$$att(\beta, \theta) = e^{-0.183 \cdot (1 - p(\beta, \theta)) \cdot p0(\beta, \theta)}$$

p is the path length to the entrance point on the body ellipse relative to p0; and
p0 is the path length to the selected point on the body ellipse.

The average relative skin exposure is then the average of the exposure for all points around the body ellipse divided by the exposure at the center of the target ROI. For the average collimated exposure, the same exposure equation is used, but with the intensity set to zero for all ray angles whose fan angle exceeds that of the range of angles spanned by the two rays that intersect the tangents to the target ellipse, i.e.:

intensity(α(β,θ))=0 if α>AC(θ) or α<ACC(θ)

AC is the clockwise angular position of the collimator leaf for source angle θ; and
ACC is the counter-clockwise angular position of the collimator leaf.

Figure 20:
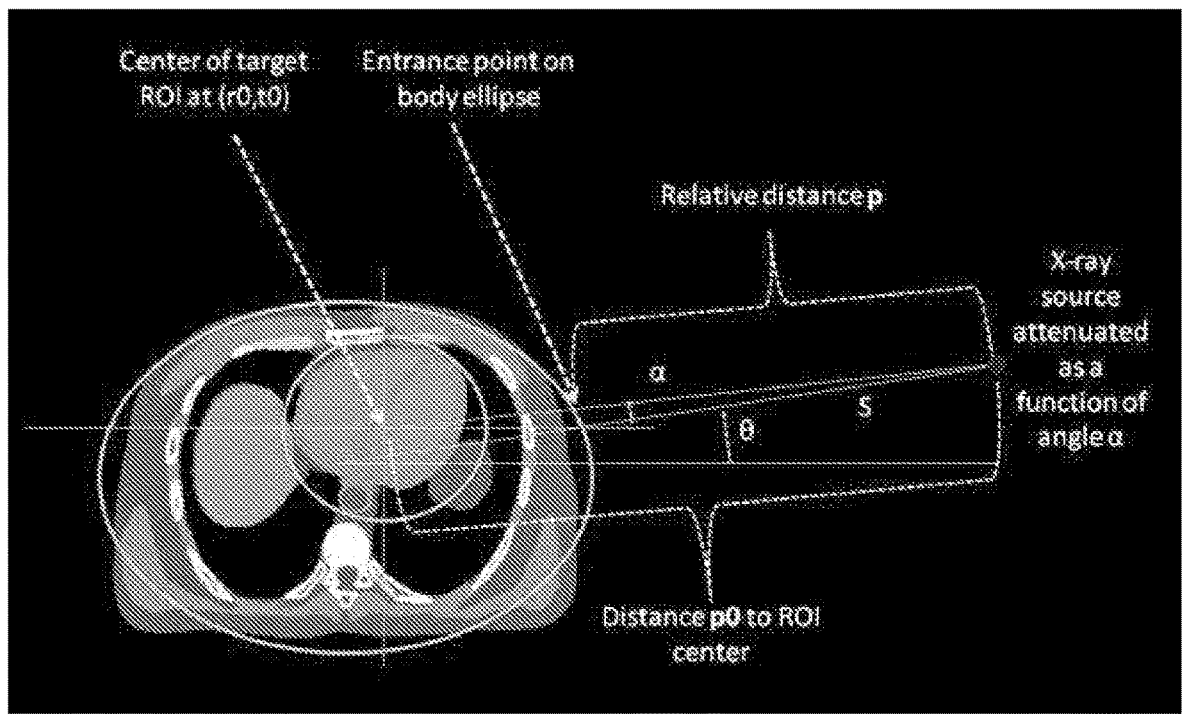
FIG. 20 illustrates geometry for a ray at angle α exposing the center of the target ROI.

Finally, the exposure at the center of the target ROI is calculated as a reference for the skin exposure values. In this case, p0 corresponds to the path length to the point at the center of the target ellipse and p is calculated as the relative path length to the point on the body ellipse (FIG. 20). As this is the center of the target ellipse, the same value applies whether or not dynamic collimation is used. FIG. 20 illustrates geometry for a ray at angle α exposing the center of the target ROI. The ray of FIG. 20 is further attenuated by the body path length $(1-p) \cdot p0$.

For the kidneys, ellipses were used to outline the target ROI and body of the patient. A single multi-slice scan was used to acquire the kidney perfusion images with the central image shown in FIG. 21. The average relative (un-collimated) skin dose was compared to the average relative (collimated) skin dose.

A second kidney study was used to not only corroborate the results of the first study, but to demonstrate the additional dose savings that would be achieved for a whole-organ kidney study. Five equally-spaced sections (FIGS. 22A-E) were selected spanning the entire kidney with the first and last sections fully collimated when utilizing dynamic collimation. The central section was used to compare with the central section of the previous study and the overall whole-organ un-collimated (relative) kidney dose was compared with the overall dynamically collimated (relative) kidney dose.

The reduction in skin exposure that can be achieved using transverse dynamic collimation of heart and kidney scans was calculated using the above-described elliptical models. The results, collimated and un-collimated exposure values relative to the average exposure calculated at the center of the target ROI, are summarized in Table 1 below:

TABLE 1

| | Un-collimated Exposure | Collimated Exposure | Exposure Reduction |
|---|---|---|---|
| Heart | 2.61 | 1.2 | 2.1:1 |
| Whole Organ | 2.605 | .704 | 3.7:1 |
| Kidney Study I | 2.545 | 1.58 | 1.61:1 |
| Kidney Study II | 2.1 | 1.0 | 2.1:1 |
| Whole Organ II | 2.1 | .584 | 3.6:1 |

These results indicate a significant skin dose reduction for both heart and kidney scans. A 3.7:1 reduction in skin exposure was calculated for the whole-heart scan. A 1.6:1 to 2.1:1 reduction in skin exposure was calculated for a kidney scan and a 3.6:1 reduction for a whole organ kidney scan (both kidneys are included in the target ROI).

The reduced skin exposure calculated for heart and kidney scans demonstrates the significant benefit of transverse dynamic collimation, especially to whole organ studies. Skin exposure values are 2.1 to 2.6 times higher than the exposure at the center of the target ROI, even with an x-ray compensator. This demonstrates how important it is to keep skin exposure values as low as possible.

Dynamic collimation to target the VOI can greatly reduce patient dose (up to 4:1 reduction in skin exposure for whole organ cardiac and kidney scans). This reduction in dose may enable coronary CT angiography to be used on a much more routine basis. Likewise, significantly reducing the dose for CT perfusion scans and whole organ kidney scans will greatly benefit the clinical use of such scans. Dynamic collimation can greatly reduce dose for other clinical applications as well.

Sampling Frequency Control

Figure 23:
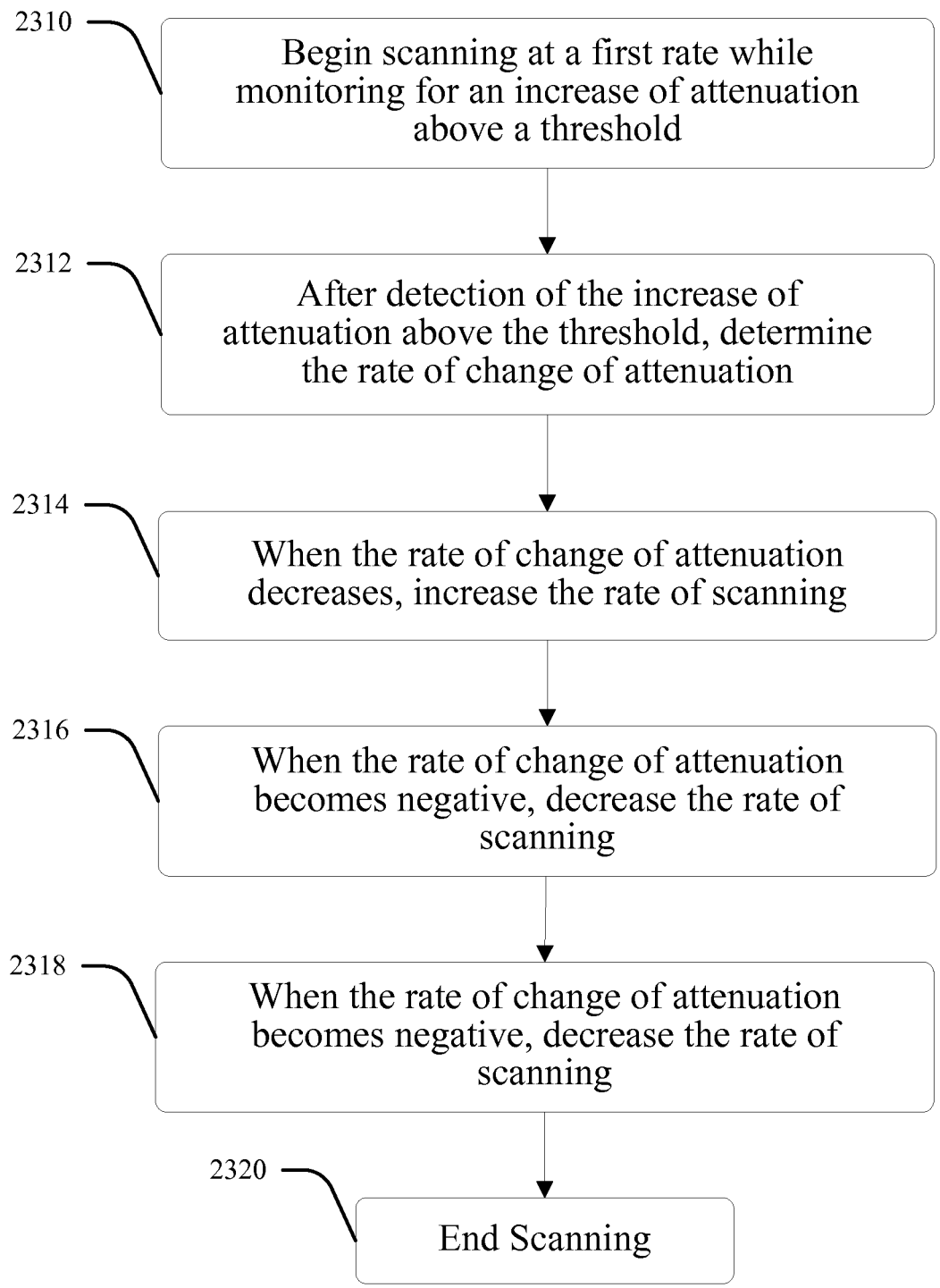
FIG. 23 illustrates a method of contrast-enhanced computed tomography (CT) imaging.
Figure 24:
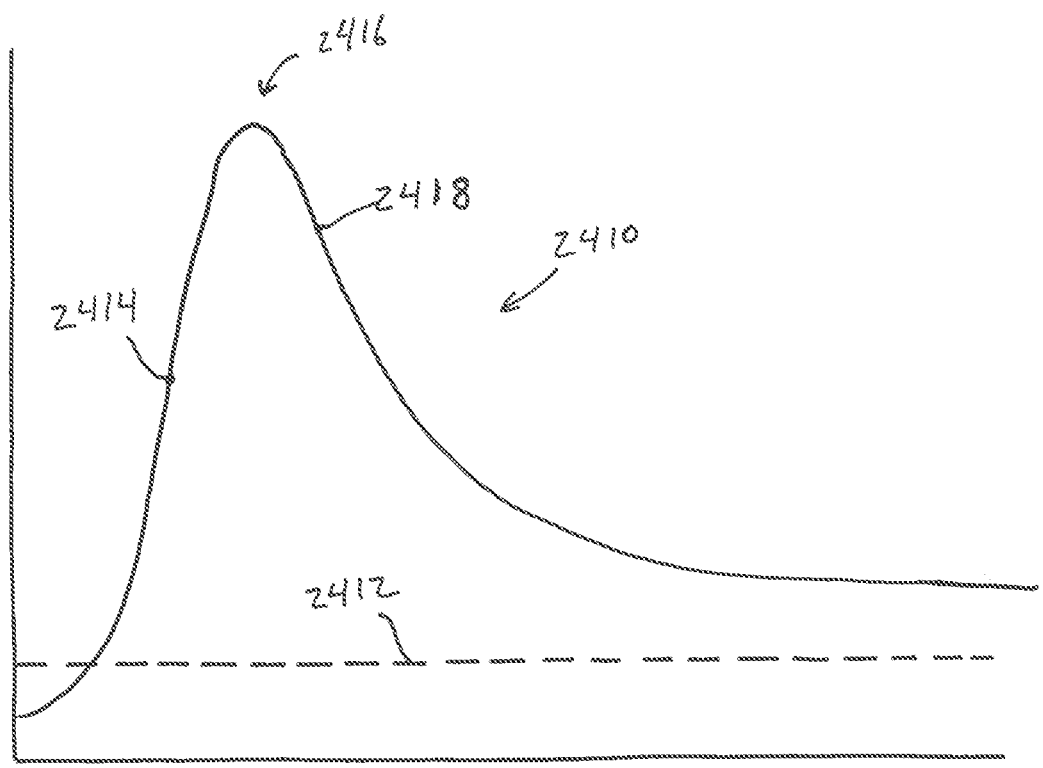
FIG. 24 schematically illustrates a curve representing a magnitude of radiation attenuation (vertical axis) by a contrast-enhanced structure over time (horizontal axis).

In some embodiments, radiation dose delivered to a patient can be reduced by varying a scanning frequency or interval between scans during a series of scans. FIG. 23 illustrates a method of contrast-enhanced computed tomography (CT) imaging. The following description of FIG. 23 refers to FIG. 24, which schematically illustrates a curve 2410 representing a magnitude of radiation attenuation (vertical axis) by a contrast-enhanced structure over time (horizontal axis), and a threshold 2412. In some embodiments, the threshold 2412 is 35 HU. In some embodiments, the threshold can be other predetermined attention densities, such as 50, 75, or 100 HU, for example. In some embodiments, the threshold comprises a degree of increase, e.g., a percentage, in the attenuation compared to a value indicated by an initial scan.

At step 2310, scanning can begin at a first rate while monitoring for an increase of attenuation above the threshold 2412. At step 2312, after detection of the increase of attenuation above the threshold, the rate of change of attenuation can be determined between scans. At step 2314, when the rate of change of attenuation decreases (corresponding to an inflection point 2414 on the ascending part of the curve 2410), the rate of scanning can be increased. At step 2316, when the rate of change of attenuation becomes negative (corresponding to a peak 2416 of the curve 2410), the rate of scanning can be decreased. In some embodiments, the frequency is reduced at step 2316, in response to detection of a decrease in attenuation. For example, the scan interval can be lengthened for a next scan upon detecting a first decrease in attenuation after the increase above the threshold 2412.

At step 2318, when the rate of change of attenuation decreases (corresponding to an inflection point 2418 on the descending part of the curve 2410), the rate of scanning can be further decreased. The rate can be further decreased in some embodiments by increasing a scan interval with each successive scan. In some embodiments, the scan interval can be approximately doubled with each successive scan.

Scanning can be terminated at step 2320 in response to expiration of a predetermined period of time, completion of a predetermined number of scans, increase of a scan interval beyond a predetermined interval, or other trigger. In some embodiments, if a remaining time between a latest scan and an end of the predetermined period is less than an interval between the latest scan and an immediately preceding scan, a penultimate scan can be performed at approximately half of the remaining time after the latest scan and a final scan can be performed at the end of the predetermined period.

Figure 25:
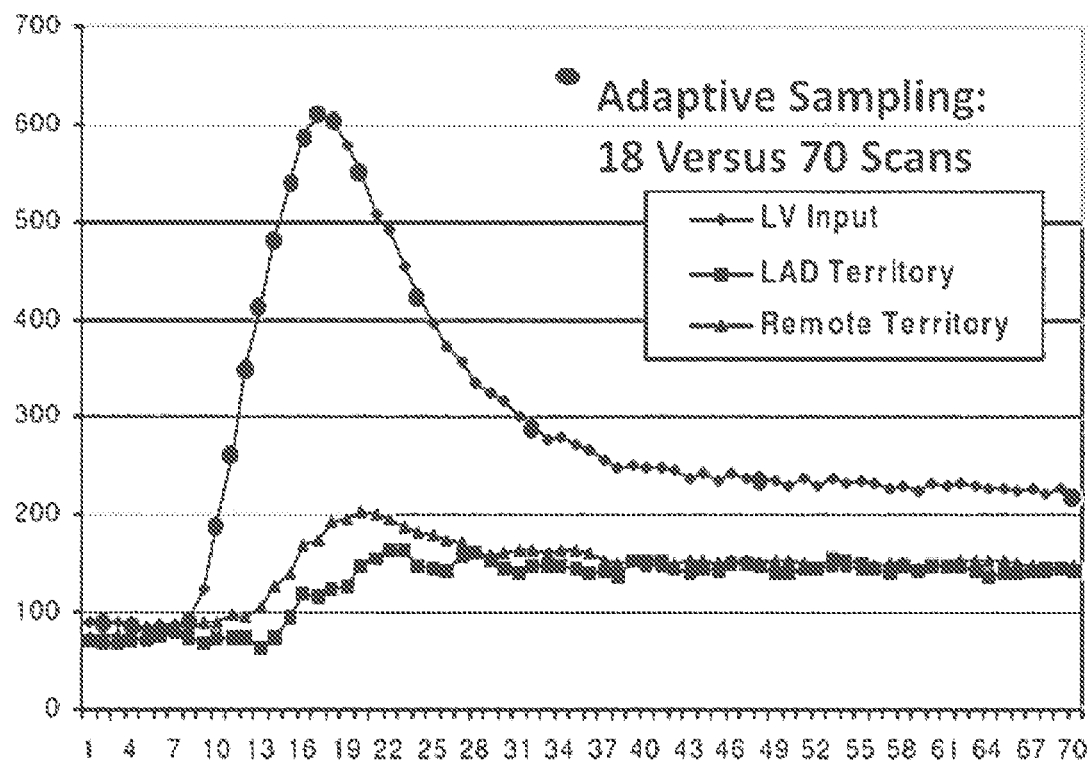
FIG. 25 is an exemplifying plot of magnitudes of radiation attenuation (vertical axis) by various contrast-enhanced structures over time (horizontal axis), and shows sampling rates and intervals according to an exemplifying embodiment.

FIG. 25 is an exemplifying plot of magnitudes of radiation attenuation by various contrast-enhanced structures over time. The vertical axis corresponds to attenuation density in Hounsfield Units. The horizontal axis corresponds to time in seconds. In FIG. 25, the large circles represent scans initiated by a sampling frequency adjustment according to an embodiment. Small circles correspond to scans obtained at each of 70 seconds. Squares in FIG. 25 represent attention through the LAD territory as detected by scans each second. FIG. 25 shows that application of a sampling frequency or interval adjustment can result in 18 scans compared to 70 scans if a scan is performed each second. Triangles in FIG. 25 represent attention through remote territory as detected by scans each second.

The methods described herein for controlling contrast-enhanced computed tomography imaging can be implemented by computer system. For example, such a system can comprise an attenuation monitoring and a scanning-frequency control module. The monitoring module can be configured to begin monitoring of the rate of change after detection of compliance of the attenuation with the threshold 2412. In some embodiments, the system can further comprise a processing module configured to generate a representation of a relationship between time and radiation attenuation by a second structure within the target region. In some embodiments, the system can further comprise a termination module configured to terminate the scanning The attenuation monitoring module can be configured to monitor, during an imaging session, an indicator of attenuation of radiation by a contrast-enhanced structure within a target region. The monitoring module can be configured to monitor a rate of change of the attenuation.

The scanning-frequency control module configured to (i) increase a frequency of scanning from a first rate to a second rate after detection of an increase of the attenuation, and (ii) decrease the frequency to a third rate after detecting a decrease in attenuation after increasing the frequency to the second rate. The scanning-frequency control module can be configured to increase the frequency to the second rate in response to detection of a decrease in a rate at which the attenuation is increasing. The scanning-frequency control module can be configured to decrease the frequency below the third rate in response to detection of a decrease in a rate at which the attenuation is decreasing. The scanning-frequency control module can be further configured to decrease the frequency further below the third rate with each successive scan. The scanning-frequency control module can be configured to divide the frequency by approximately two with each successive scan. The scanning-frequency control module can be configured to reduce the frequency to the third rate upon a first detection of a decrease in attenuation after an increase to the second rate.

The termination module can be configured after a predetermined period of time and direct performance of a final scan at the end of the predetermined period. The termination module can be configured to terminate the scanning after a predetermined period of time, and, if a remaining time between a latest scan and an end of the predetermined period is less than an interval between the latest scan and an immediately preceding scan, direct performance of (i) a penultimate scan at a half of the remaining time after the latest scan and (ii) a final scan at the end of the predetermined period.

Radiation Exposure Control

Figure 26:
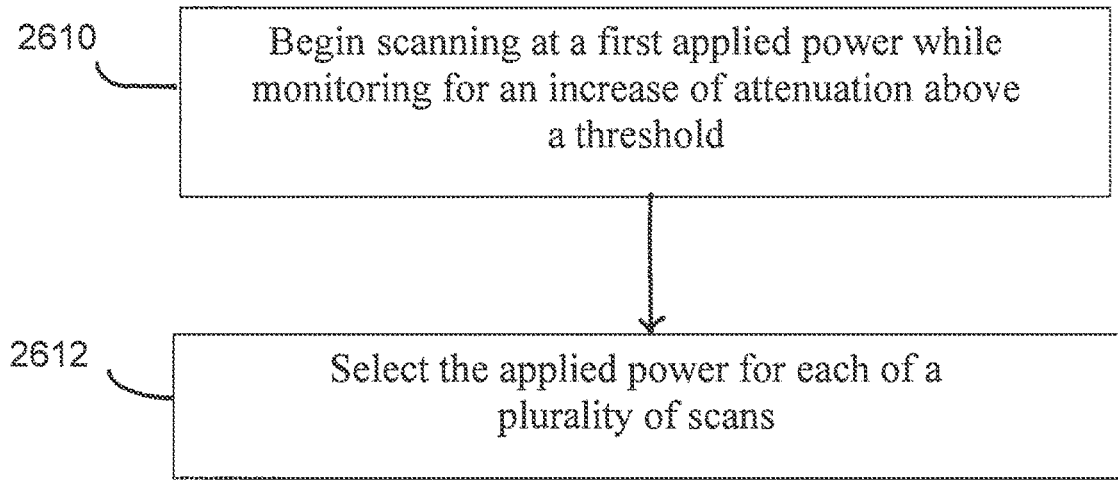
FIG. 26 illustrates a method of contrast-enhanced computed tomography (CT) imaging.

In some embodiments, radiation dose delivered to a patient can be reduced by varying an applied power during a series of scans. FIG. 26 illustrates a method of contrast-enhanced computed tomography (CT) imaging. At step 2610, scanning can be at a first applied power while monitoring for an increase of attenuation above the threshold 2412. At step 2612, the applied power for each of a plurality of scans can be selected. The applied power can be varied among scans of a series during a session.

The applied power can be determined, at least in part, by selection of an applied current. In some embodiments, the applied power can be varied by changing an applied voltage or a resistance. In some embodiments, the power for a first scan can be a maximum power applied during the session. In some embodiments, a current applied to a first scan can be about 200 ma. The applied power can be selected in some embodiments by multiplying a maximum current by an exponential function based on the attenuation determined from the preceding scan. In some embodiments, the exponential function can yield a value that is (i) greater than a minimum allowable current divided by a maximum allowable current, and (ii) less than 1. In some embodiments, the exponential function can be function F determined by $$F = e^{C \cdot (TH - \Delta HU)/TH}$$

wherein TH is a threshold attenuation magnitude and ΔHU is equal to a difference in magnitude, in Hounsfield Units, between the attenuation determined from a preceding scan and a baseline attenuation. The baseline attenuation can be a magnitude of the attenuation indicated based on the initial scan.

In some embodiments, C is selected such that, when the function is applied, an applied current for a next scan is about a tenth of the maximum allowable current when the attenuation of the preceding scan is about ten times above the threshold attenuation magnitude. In some embodiments, C can be about 0.25.

Figure 27:
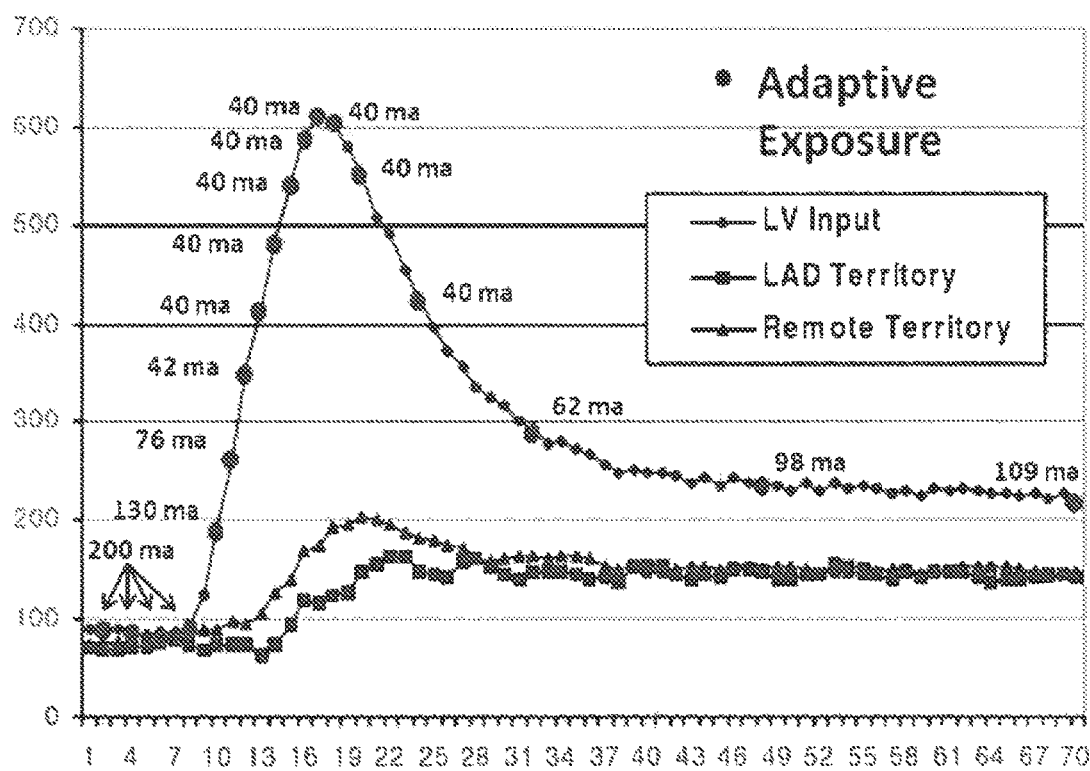
FIG. 27 is an exemplifying plot of magnitudes of radiation attenuation (vertical axis) by various contrast-enhanced structures over time (horizontal axis), and indicates a current magnitude for a plurality of scans.

FIG. 27 is an exemplifying plot, similar to FIG. 25, of magnitudes of radiation attenuation by various contrast-enhanced structures over time, and indicates a current magnitude for a plurality of scans. The vertical axis corresponds to attenuation density in Hounsfield Units. The horizontal axis corresponds to time in seconds. In FIG. 27, each large circle represents a scan and an applied current is identified for each large circle. As shown by FIG. 27, an applied power corresponding to a minimum allowable current can be selected for each scan for which a determining function, such as the function F for example, indicates, based on the attenuation indicated by a preceding scan, a current less than the minimum allowable current.

The methods described herein for controlling contrast-enhanced computed tomography imaging can be implemented by computer system. For example, such a system can comprise an attenuation monitoring and a power control module. In some embodiments, the system can comprise a power control module in addition or alternative to a scanning-frequency control module. The power control module can be configured to select an applied power for each of a plurality of scans based on the attenuation detected from a preceding scan. The power control module can be configured to direct application of a maximum power applied during the session in a first scan. The power control module can be configured to apply substantially the same amount of power to individual scans until detection of an increase of the attenuation to or beyond a threshold attenuation magnitude. The power control module can be configured to select the applied power by multiplying a maximum current by an exponential function, such as described above.

Additional Methods

The statistics for perfusion curves can be improved with a number of slices used for a VOI. Thus, in some embodiments, a VOI can utilize more than one slice. Motion may occur between the reference scan and perfusion series. Registration can be performed for the tissues containing the VOIs. Motion correction can be performed between all images acquired in the series. In some embodiments, motion correction can significantly improve the quality and accuracy of the perfusion curves. For example, motion can occur because of breathing as indicated by the oscillations repeating approximately every three seconds in the LAD territory data of FIGS. 25 and 27. In some embodiments, motion control can permit further dose reduction while retaining statistical accuracy of the perfusion curves and achieving comparable diagnostic results.

Example of Dosage Reduction Using Scan Frequency Control

A kidney perfusion study was performed applying an embodiment of scan frequency control.

Figure 21:
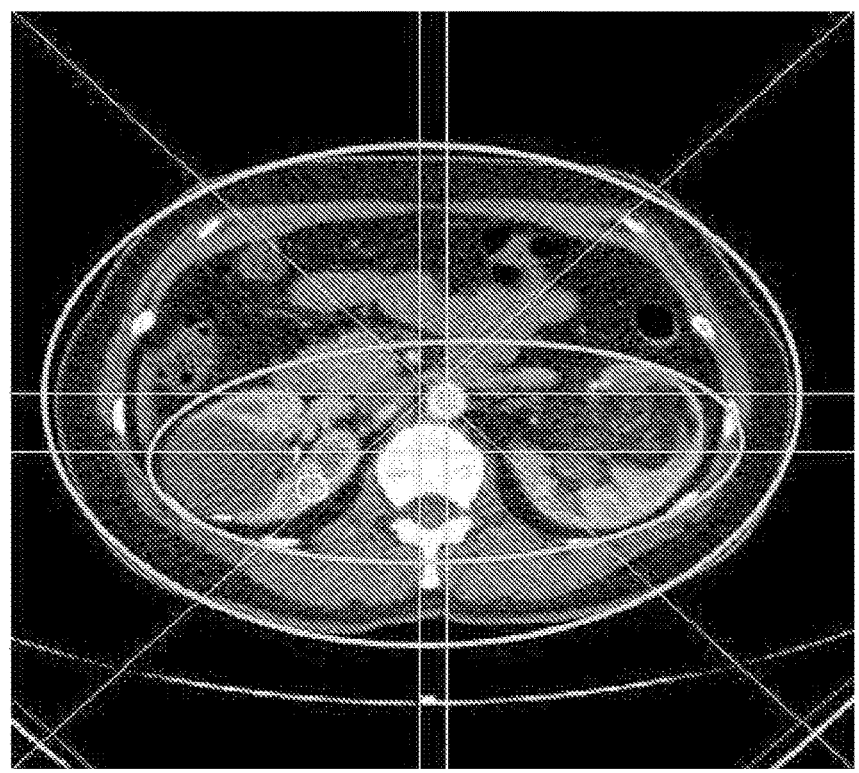
FIG. 21 shows a central kidney cross-section showing ellipses defining the outline of the body and target ROI including both kidneys with reference lines.

Kidney perfusion data was acquired using a first protocol. In the first protocol, a low dose reference scan was performed. From the reference scan, an axial location and extent of the scan was identified for a perfusion series. The target ROIs were identified. A 60-second scan series was performed, with each scan being acquired with a tube current of 200 ma. One scan was performed each second for 60 seconds. Each scan was directed to a 8 cm circular ROI. FIG. 21 illustrates a slice obtained from a first person using the first protocol. From the slice shown in FIG. 21, various perfusion parameters were determined, including mean arterial transit time (MTTa), renal plasma flow (RPF), and glomerular filtration rate (GFR). These parameters are shown in Table 2A, below, as "fully-sampled data."

Sub-sampled data was obtained by applying a second (emulated) protocol to select a subset of data from the fully-sampled data. According to the second protocol, a low dose reference scan would be performed. From the reference scan, the axial location and extent of the scan would be identified as well as the arterial VOI used to define the motion of a transverse dynamic collimator. The target ROIs would be identified. The sub-sampled data was selected as though a 60-second scan series had been performed with the scanning frequency being adjusted during the series as data indicative of the arterial input function (AIF) was acquired.

Figure 28:
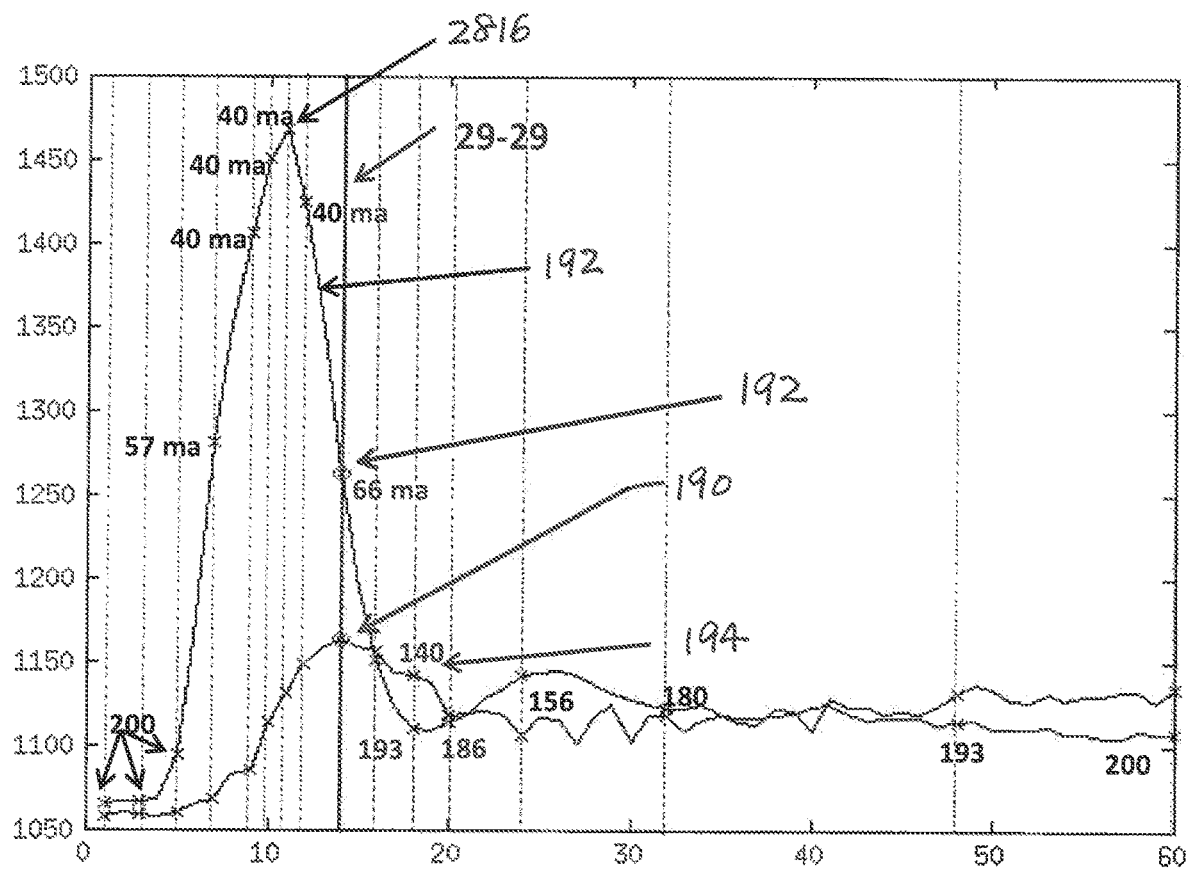
FIG. 28 is an exemplifying plot of magnitudes of radiation attenuation (vertical axis) by various contrast-enhanced structures over time (horizontal axis), and indicates a current magnitude for a plurality of scans.
Figure 29:
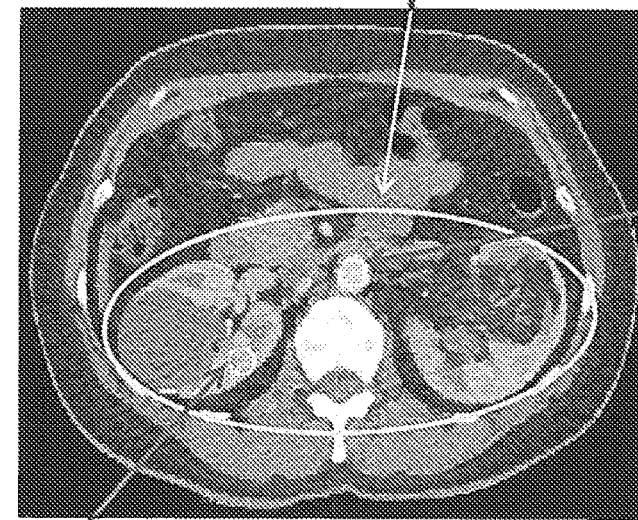
FIG. 29 is an image corresponding to a scan from a series of scans indicated in FIG. 28.

A sampling algorithm was applied in the second (emulated) protocol. The sampling algorithm adaptively varied the sampling along the arterial input function (AIF) which corresponds, to blood flow in the aorta. FIGS. 28 and 29 illustrate the adaptive sampling based on the AIF. The second protocol was applied to select the sub-sampled data from the fully-sampled data as though following steps had been preformed in capturing the data. A first scan took place at time t=0. Another scan was performed every two seconds after the first scan until the arterial curve rose above a predefined threshold TH, e.g. 35 HU. After the curve rose above the threshold, the slope of the curve was tracked using a finite difference. When the magnitude of the slope was found to have decreased, the interval between scans was reduced such that one scan was performed every second. When the peak of the arterial curve was detected by the value of the slope becoming negative, the scanning frequency was made one scan every 2 seconds. After the inflection point of descent of the curve was detected by the magnitude of the slope again decreasing, the scan interval was doubled after each subsequent scan. Very sparse sampling can be performed over the slowly descending exponential portion of the curve. At the end of a predetermined scan period, one final scan was performed to complete the sampling of the arterial curve.

FIG. 29 illustrates the ROI 144 for the second (emulated) protocol. FIG. 28 includes curves 190, 192, 194 corresponding respectively to attenuation by cortex 186, aorta 188, and kidney tissue, shown in FIG. 29. FIG. 28 indicates 16 subsamples chosen out of 60. Each subsample is represented by a vertical line intersecting an "x." FIG. 29 corresponds to a subsample 29-29 in FIG. 28. Current magnitudes are indicated in FIG. 28 for each subsample. The minimum current was 40 ma, occurring at the peak 2816 of the AIF curve, and the maximum current was 200 ma, used at the beginning of the scan.

From the data obtained using the second (emulated) protocol, various perfusion parameters were determined, including mean arterial transit time (MTTa), renal plasma flow (RPF), and glomerular filtration rate (GFR). These parameters are shown in Table 2A, below, as "sub-sampled data." The structures within the ROIs that were used to generate the curves used to calculate these parameters included the cortex of the kidney and aorta. The parameters derived from the original fully-sampled data are compared to those derived from the sparsely-sampled (frequency adjusted) data in Table 2A.

The kidney perfusion study compared MTTa/RPF/GFR values between original fully-sampled values and values obtained using sub-sampled data. Table 2A summarizes the results of the comparison. Maximum deviation in MTTa|RPF|GFR values is 5%.

TABLE 2A

| | MTTa/RPF/GFR |
|---|---|
| Fully-sampled data | 8.5\|144\|34 |
| Sub-sampled data | 8.3\|141\|36 |

Figure 22A:
FIGS. 22A-E show five equally-spaced kidney cross-sections showing body outlines and target ROIs including both kidneys with reference lines.
Figure 22D:
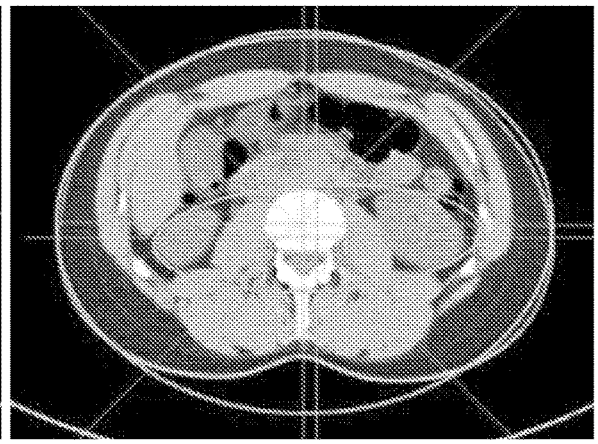
Figure 22B:
Figure 22E:
Figure 22C:
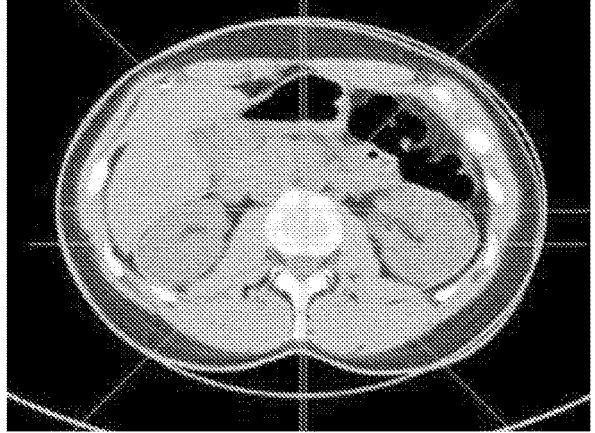

The slice obtained from the first person shown in FIG. 21 (Case I) and a slice obtained from a second person shown in FIG. 22C (Case II) were used to estimate the dosage reduction that would be obtained though use of sparse sampling, modulated tube current, and dynamic collimation to the ROI (an elliptical region surrounding both kidneys and aorta). Those estimates were compared to the radiation exposure without sparse sampling, modulated tube current, and dynamic collimation to the ROI. The overall exposure reductions were also calculated and compared.

The dosage reduction from sub-sampling was determined based on application of the second (emulated) protocol, described above. The dosage reduction from dynamic collimation was calculated using the calculation techniques described above under the heading "Dynamic Transverse Collimation Dose Reduction."

The average exposure due to modulated tube current was used to determine the dosage reduction from modulation of tube current. For both Case I and Case II, a scan-exposure algorithm was applied to calculate the exposure reduction that would have been attributable to current modulation had the algorithm been applied during data acquisition. The scan-exposure algorithm would have adaptively varied the input current and, therefore, the emitted radiation during scanning. FIGS. 25 and 27 illustrate adaptive scan-exposure control based on the AIF. Given a maximum and a minimum current (ma) allowed, exposure was calculated as though the following scan-exposure algorithm and procedure had been used to acquire the data. Scans were performed at the maximum current, e.g. 200 ma, until the arterial curve was detected to have risen above the threshold. Thereafter, the applied current was reduced, using the predetermined contrast detection threshold TH, by multiplying the maximum current by the following factor F:

$$F = e^{C \cdot (TH - \Delta HU)/TH}$$

where:
C=0.25
(minimum allowable ma)/(maximum ma)<F<1
$\Delta HU$=the difference of the Hounsfield Unit value of the curve and the baseline value corresponding to the first HU value of the curve.

C was chosen such that if the arterial curve rose 10 times above the threshold TH (e.g., 35 HU), the current would be reduced by 0.1. For example, if the attenuation is 275 HU and the baseline is 100 HU ($\Delta HU$=175), then the current would be decreased from a maximum of 200 ma to 40 ma. The applied x-ray current was determined for the remaining scans using this formula above for the rest of the series.

Table 2B summarizes the exposure reductions calculated from evaluation of Case I and Case II. The average overall reduction for Case I and Case II is 10.5:1.

TABLE 2B

| | Case I | Case II |
|---|---|---|
| Sub-sampling Exposure Reduction | 3.8:1 | 3.8:1 |
| Current Modulation Exposure Reduction | 1.5:1 | 1.5:1 |
| Dynamic Collimation Reduction | 1.6:1 | 2.1:1 |
| Overall Reduction | 9.1:1 | 12:1 |

Based on the results of this comparison, the second protocol can provide diagnostic results comparable to the first protocol. For kidney perfusion scans, the radiation dose using the second protocol can be expected to be one-tenth of the radiation dose to the patient using the first protocol.

Figure 30:
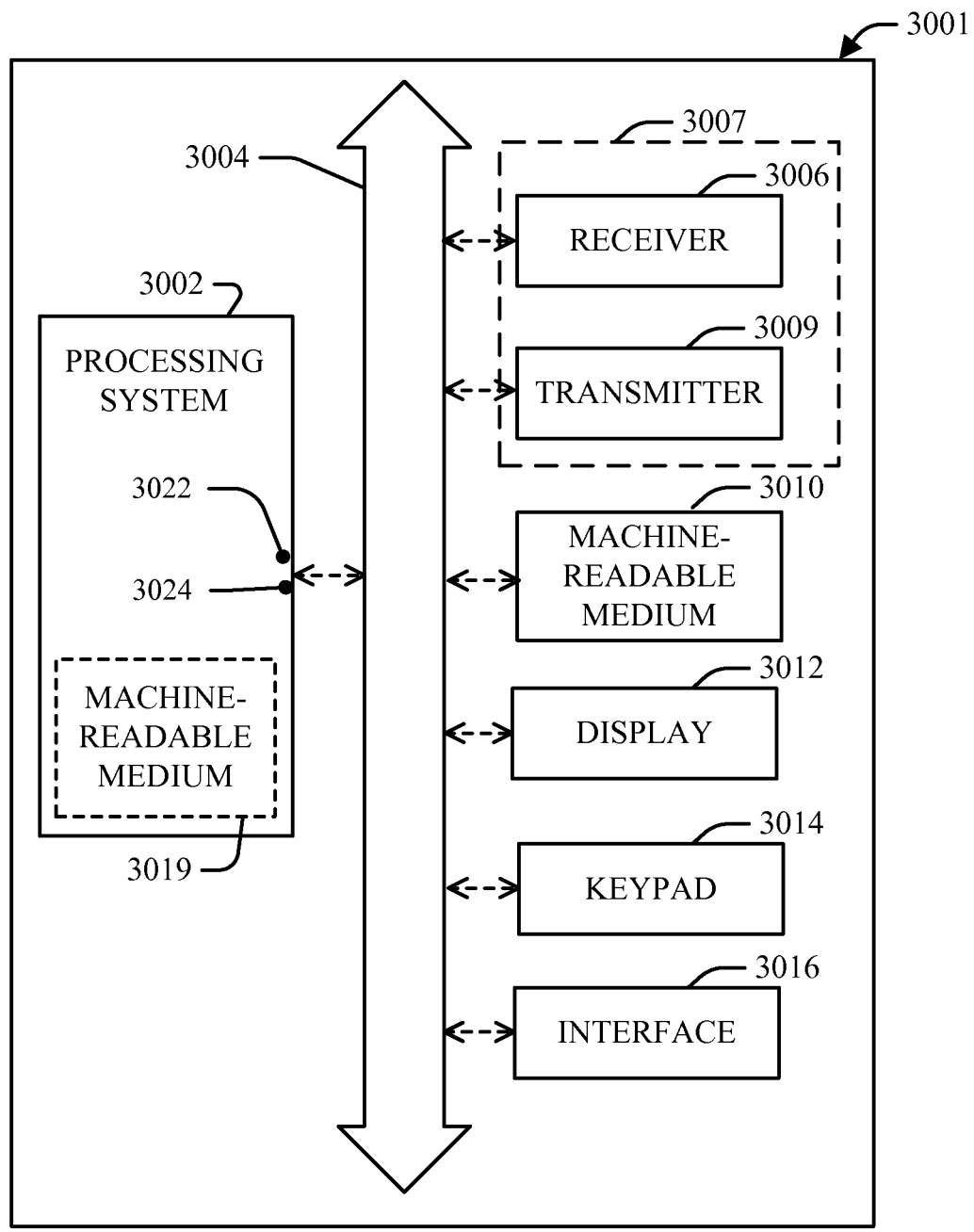
FIG. 30 is a diagram illustrating an exemplifying system, including a processor and other internal components, according to an aspect of the subject technology

FIG. 30 is a conceptual block diagram illustrating an example of a system, in accordance with various aspects of the subject technology. A system 3001 may be, for example, a client device or a server. The system 3001 may include a processing system 3002. The processing system 3002 is capable of communication with a receiver 3006 and a transmitter 3009 through a bus 3004 or other structures or devices. It should be understood that communication means other than busses can be utilized with the disclosed configurations. The processing system 3002 can generate audio, video, multimedia, and/or other types of data to be provided to the transmitter 3009 for communication. In addition, audio, video, multimedia, and/or other types of data can be received at the receiver 3006, and processed by the processing system 3002.

The processing system 3002 may include a processor for executing instructions and may further include a machine-readable medium 3019, such as a volatile or non-volatile memory, for storing data and/or instructions for software programs. The instructions, which may be stored in a machine-readable medium 3010 and/or 3019, may be executed by the processing system 3002 to control and manage access to the various networks, as well as provide other communication and processing functions. The instructions may also include instructions executed by the processing system 3002 for various user interface devices, such as a display 3012 and a keypad 3014. The processing system 3002 may include an input port 3022 and an output port 3024. Each of the input port 3022 and the output port 3024 may include one or more ports. The input port 3022 and the output port 3024 may be the same port (e.g., a bi-directional port) or may be different ports.

The processing system 3002 may be implemented using software, hardware, or a combination of both. By way of example, the processing system 3002 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 3019) may include storage integrated into a processing system, such as might be the case with an ASIC. Machine-readable media (e.g., 3010) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 3002. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer pro gram including code.

An interface 3016 may be any type of interface and may reside between any of the components shown in FIG. 30. An interface 3016 may also be, for example, an interface to the outside world (e.g., an Internet network interface). A transceiver block 3007 may represent one or more transceivers, and each transceiver may include a receiver 3006 and a transmitter 3009. A functionality implemented in a processing system 3002 may be implemented in a portion of a receiver 3006, a portion of a transmitter 3009, a portion of a machine-readable medium 3010, a portion of a display 3012, a portion of a keypad 3014, or a portion of an interface 3016, and vice versa.

Figure 31:
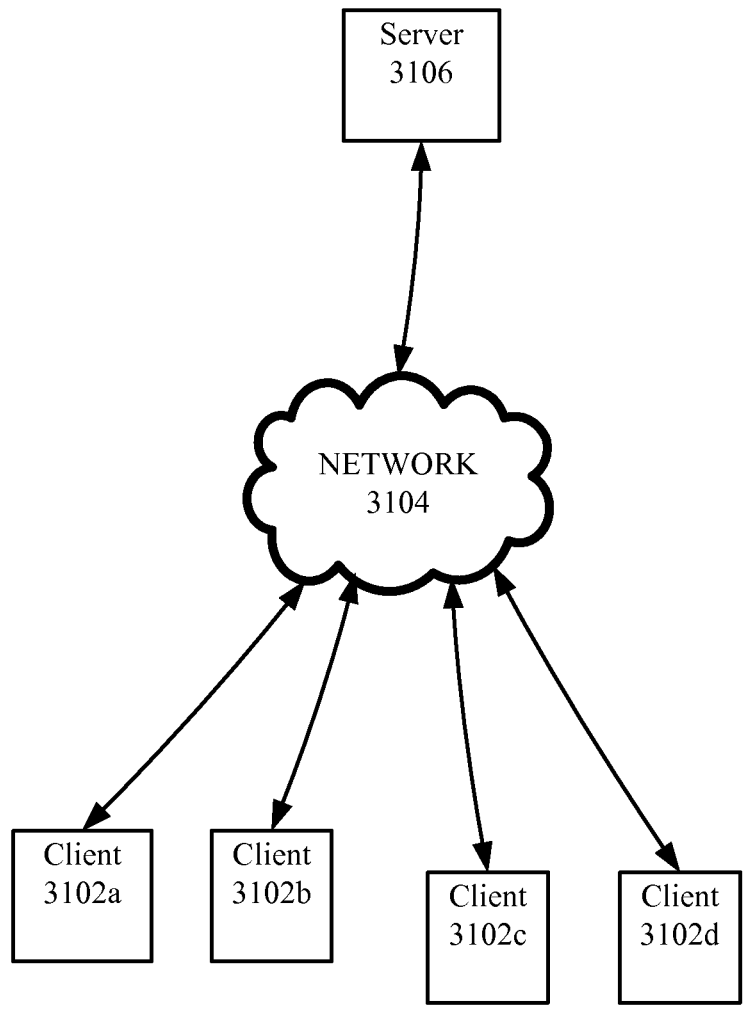
FIG. 31 is a diagram illustrating an exemplary communication between a server and a client machine according to an aspect of the subject technology.

FIG. 31 illustrates a simplified diagram of a system 3100, in accordance with various embodiments of the subject technology. The system 3100 may include one or more remote client devices 3102 (e.g., client devices 3102a, 3102b, 3102c, and 3102d) in communication with a server computing device 3106 (server) via a network 3104. In some embodiments, the server 3106 is configured to run applications that may be accessed and controlled at the client devices 3102. For example, a user at a client device 3102 may use a web browser to access and control an application running on the server 3106 over the network 3104. In some embodiments, the server 3106 is configured to allow remote sessions (e.g., remote desktop sessions) wherein users can access applications and files on the server 3106 by logging onto the server 3106 from a client device 3102. Such a connection may be established using any of several well-known techniques such as the Remote Desktop Protocol (RDP) on a Windows-based server.

By way of illustration and not limitation, in one aspect of the disclosure, stated from a perspective of a server side (treating a server as a local device and treating a client device as a remote device), a server application is executed (or runs) at a server 3106. While a remote client device 3102 may receive and display a view of the server application on a display local to the remote client device 3102, the remote client device 3102 does not execute (or run) the server application at the remote client device 3102. Stated in another way from a perspective of the client side (treating a server as remote device and treating a client device as a local device), a remote application is executed (or runs) at a remote server 3106.

By way of illustration and not limitation, a client device 3102 can represent a computer, a mobile phone, a laptop computer, a thin client device, a personal digital assistant (PDA), a portable computing device, or a suitable device with a processor. In one example, a client device 3102 is a smartphone (e.g., iPhone, Android phone, Blackberry, etc.). In certain configurations, a client device 3102 can represent an audio player, a game console, a camera, a camcorder, an audio device, a video device, a multimedia device, or a device capable of supporting a connection to a remote server. In one example, a client device 3102 can be mobile. In another example, a client device 3102 can be stationary. According to one aspect of the disclosure, a client device 3102 may be a device having at least a processor and memory, where the total amount of memory of the client device 3102 could be less than the total amount of memory in a server 3106. In one example, a client device 3102 does not have a hard disk. In one aspect, a client device 3102 has a display smaller than a display supported by a server 3106. In one aspect, a client device may include one or more client devices.

In some embodiments, a server 3106 may represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server 3106 can be stationary. In some embodiments, a server 3106 can be mobile. In certain configurations, a server 3106 may be any device that can represent a client device. In some embodiments, a server 3106 may include one or more servers.

In one example, a first device is remote to a second device when the first device is not directly connected to the second device. In one example, a first remote device may be connected to a second device over a communication network such as a Local Area Network (LAN), a Wide Area Network (WAN), and/or other network.

When a client device 3102 and a server 3106 are remote with respect to each other, a client device 3102 may connect to a server 3106 over a network 3104, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network 3104 can be a LAN network, a WAN network, a wireless network, the Internet, an intranet or other network. A network 3104 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name or other system name. These illustrate some examples as to how one device may be remote to another device. But the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or vice versa.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A collimator for a computed x-ray tomography imaging device, comprising a first grating and a second grating positioned on opposing sides of a primary radiation delivery window, the first and second gratings being part of separate first and second leaves, each of the first and second gratings comprising a plurality of attenuating members with a plurality of secondary radiation delivery windows extending between adjacent attenuating members of the first grating and the second grating, respectively, and wherein a width of each attenuating member is proportional to a distance between the attenuating member and the primary window, and the first and second gratings are each adapted to receive x-rays from a single x-ray source.

2. The collimator of claim 1, wherein a width of each secondary window is less than a width of the primary window.

3. The collimator of claim 1, wherein a total area of each of the plurality of secondary windows is less than a total area of the primary window.

4. The collimator of claim 1, wherein a width of each secondary window is proportional to a distance between the secondary window and the primary window.

5. The collimator of claim 4, wherein the width of each secondary window is linearly proportional to the distance between the secondary window and the primary window.

6. The collimator of claim 1, wherein the width of each attenuating member is linearly proportional to the distance between the attenuating member and the primary window.

7. The collimator of claim 1, wherein the secondary windows comprise open passages.

8. The collimator of claim 1, wherein the secondary windows comprise panes of substantially radio-transmissive material.

9. The collimator of claim 1, wherein the attenuating members are oriented generally parallel to sides of the primary window.

10. The collimator of claim 1, wherein the secondary windows are oriented generally parallel to sides of the primary window.

11. The collimator of claim 1, wherein the first grating is movable relative to the second grating.

12. The collimator of claim 11, wherein the first and second gratings are independently movable.

13. A method of directing radiation during computed tomography (CT) imaging, comprising:
    emitting x-ray radiation from a radiation source toward an object;
    passing a first portion of the radiation through a primary window toward a target region in the object;
    passing a second portion of the radiation through an adjacent attenuating member on each of opposing sides of the primary window, to corresponding regions in the object outside the target region;
    rotating the radiation source and the primary window and the adjacent attenuating members about an axis, and independently translating the adjacent attenuating members relative to the primary window in a direction non-parallel to the axis; and
    generating CT image data based on the first and second portions of the radiation.

14. The method of claim 13, further comprising attenuating, between the primary window and a secondary window, at least a third portion of the radiation.

15. The method of claim 14, wherein the attenuating comprises blocking passage of at least the third portion of the radiation between the primary and secondary windows.

16. The method of claim 13, further comprising rotating the radiation source and the primary window and adjacent attenuating members about an axis, and wherein radiation is passed through the primary window and the adjacent attenuating members while either (i) centers of the primary window and at least two adjacent attenuating members lie in a plane non-parallel to the axis or (ii) a plane intersecting the centers and the axis is non-parallel to the axis.

17. The method of claim 13, further comprising rotating the radiation source, the primary window, and the adjacent attenuating members about an axis, and translating the adjacent attenuating members relative to the primary window in a direction non-parallel to the axis.

18. The method of claim 17, wherein the adjacent attenuating members are translated relative to the primary window during rotation of the radiation source.

19. The method of claim 18, wherein a first of the adjacent attenuating members is translated independently of a second of the adjacent attenuating members on an opposing side of the primary window from the first of the adjacent attenuating members.

20. The method of claim 13, wherein the independently translating corresponds to variations in an outline of the target region.

21. The method of claim 13, wherein the independently translating includes axial translation and transverse translation.

22. The method of claim 13, wherein a width of the primary window is greater than a width of the adjacent attenuating members.

23. The method of claim 13, wherein the generating CT image data also includes obtaining attenuation information from outside the target region.

* * * * *